US012691241B2

(12) United States Patent
   Dawson

(10) Patent No.: US 12,691,241 B2
(45) Date of Patent: Jul. 28, 2026

(54) BREATHING ASSISTANCE APPARATUS

(71) Applicant: OPSEL PTY LTD, Attadale (AU)

(72) Inventor: Peter Dawson, Attadale (AU)

(73) Assignee: Opsel Pty Ltd, Attadale (AU)

( * ) Notice: Subject to any disclaimer, the term of this patent is extended or adjusted under 35 U.S.C. 154(b) by 448 days.

(21) Appl. No.: 18/566,784

(22) PCT Filed: Oct. 6, 2021

(86) PCT No.: PCT/AU2021/051161
   § 371 (c)(1),
   (2) Date: Dec. 4, 2023

(87) PCT Pub. No.: WO2022/261695
   PCT Pub. Date: Dec. 22, 2022

(65) Prior Publication Data
   US 2024/0277963 A1      Aug. 22, 2024

(30) Foreign Application Priority Data
   Jun. 14, 2021   (AU) ................................ 2021901778

(51) Int. Cl.
   *A61M 16/06*       (2006.01)
   *A61F 5/56*        (2006.01)
   *A61M 16/08*       (2006.01)

(52) U.S. Cl.
   CPC ........... *A61M 16/0605* (2014.02); *A61F 5/56*
      (2013.01); *A61F 5/566* (2013.01); *A61M*
      *16/0683* (2013.01); *A61M 16/0875* (2013.01);
      *A61M 2016/0661* (2013.01); *A61M 2207/10*
      (2013.01); *A61M 2210/0618* (2013.01); *A61M*
                     *2210/0625* (2013.01)

(58) Field of Classification Search
   CPC ........... A61M 16/0605; A61M 16/0683–0688;
      A61M 16/0875; A61M 2016/0661; A61M
      2207/10; A61M 2210/0618; A61M
      2210/0625; A61M 2016/0027; A61M
      2016/0033; A61M 2205/0272; A61M
      2205/3375; A61M 2205/3553; A61M
      2207/00; A61M 2209/04; A61M 2230/06;
      A61M 2230/205; A61M 2230/00; A61C
      7/08; A61F 5/56; A61F 5/566
   See application file for complete search history.

(56) References Cited

U.S. PATENT DOCUMENTS

| | | | |
|---|---|---|---|
| 8,042,542 B2 | 10/2011 | Ging et al. | |
| 2008/0173312 A1 | 7/2008 | Peake et al. | |
| 2010/0311003 A1* | 12/2010 | Kozlov | A61F 5/566 |
| | | | 128/848 |
| 2018/0147084 A1 | 5/2018 | Thornton et al. | |
| 2020/0138622 A1 | 5/2020 | Thornton et al. | |
| 2021/0322705 A1* | 10/2021 | Hasegawa | A61M 16/0688 |

* cited by examiner

*Primary Examiner* — Elliot S Ruddie
(74) *Attorney, Agent, or Firm* — Carrier, Shende & Associates P.C.; Fulchand P. Shende; Joseph P. Carrier

(57) ABSTRACT

A breathing assistance apparatus comprises an oral appliance, wherein the oral appliance has at least an uppermost splint adapted to engage with a set of maxillary teeth. The apparatus also comprises a strapless positive airway pressure nasal mask and a plurality of ferromagnetic members provided on the oral appliance and nasal mask. The ferromagnetic members comprise one or more magnets such that the nasal mask and oral appliance are attracted to each other when the apparatus is being worn by a user.

20 Claims, 23 Drawing Sheets

20

22

BREATHING ASSISTANCE APPARATUS

FIELD

The present invention relates to medical devices and, more particularly, to a breathing assistance apparatus.

BACKGROUND

Breathing disorders can cause a person to suffer from obstructive sleep apnoea (OSA) and/or chronic snoring when they are sleeping. A variety of devices are available that seek to augment a person's breathing to alleviate the foregoing problems. For example, continuous and variable positive airway pressure (PAP) devices are often prescribed to person's suffering from OSA. These devices typically comprise a nasal mask, or a full face mask, that supplies a stream of compressed air via a hose into the nostrils and/or mouth of the user at a pressure that is greater than atmospheric pressure. The pressurised air splints the airway of the person such that it is kept open, thus reducing the effects of OSA.

PAP masks suffer from various problems that can ultimately lead to non compliance by the user over time. For example, to work effectively a PAP mask must provide an airtight seal around the person's nostrils and/or mouth to maintain the pressurised airflow. The mask must, therefore, be held securely in place which is achieved by a set of elastic straps that extend from the mask around the user's head. The straps are cumbersome to handle and are uncomfortable to wear. The forces exerted by the mask when pressing against the user's face are also uncomfortable. Full-face PAP masks are, in particular, large, cumbersome devices that are not practical to wear when sleeping. Mask leakage and associated discomfort are the main contributors of failed PAP therapy.

A nasal PAP masks comprise a hose that supplies compressed air out of a pair of outlets. The two outlets are secured in position immediately underneath the nostrils of the user and deliver two separate streams of air into the nose, one for each nostril. Nasal masks of this configuration do not encourage the natural inhalation of air into the user's nose. In particular, the air flows out of the two outlets in a forced and directed manner which does not align with natural nasal breathing. Furthermore, in most persons, some natural variations in the breathing of air into their nostrils occurs. The rate of air that can be inhaled into each nostril typically differs and, in some cases, one of the nostrils may be partially or completely blocked. Nasal masks fail to accommodate these variations in breathing across the nostrils.

Oral appliances may also be prescribed to person's suffering from OSA. These devices, which are commonly called mandibular advancement splints (MAS), comprise uppermost and lowermost splints that engage with the user's maxillary and mandibular teeth respectively. The splints are held in relative position such that the lowermost splint provides for mandibular advancement of the user. The mechanical protrusion of the user's mandibular (lower) jaw increases the patient's pharyngeal space and decreases air turbulence, thus improving the ability to exchange air during sleep.

Traditionally, patients with moderate to severe OSA are issued with PAP devices, whereas patients diagnosed with mild to moderate OSA are typically issued MAS devices. PAP devices act as pneumatic stents whilst MAS devices, when properly titrated, physically increase airway space. PAP devices, whilst efficacious, are poorly tolerated and for long periods during the night are often not worn. Numerous studies that show long term compliance rates for PAP devices over five years are at about 50%. MAS devices are less effective yet can be comfortably worn for long periods of time by patients, so the net therapeutic benefit of both devices is similar. Usually by default, MAS devices are offered after initial rejection of PAP therapy.

It is to be understood that, if any prior art is referred to herein, such reference does not constitute an admission that the prior art forms a part of the common general knowledge in the art, in Australia or any other country.

SUMMARY

According to the present invention, there is provided a breathing assistance apparatus, comprising:

an oral appliance having at least an uppermost splint adapted to engage with a set of maxillary teeth;

a strapless positive airway pressure nasal mask; and a plurality of ferromagnetic elements or materials provided, or incorporated into, each of on the oral appliance and nasal mask, wherein one or more of the ferromagnetic elements or materials is or are magnetic such that the nasal mask and oral appliance are attracted to each other when the apparatus is being worn by a user of the apparatus.

The ferromagnetic elements or materials may comprise at least first and second magnetic elements or materials provided on, respectively, the oral appliance and the nasal mask respectively, wherein the first and second magnetic elements or materials are relatively arranged such that opposed magnetic poles of the first and second materials are attracted to one another between the nasal mask and oral appliance.

The apparatus may comprise first and second sets of magnetic elements or materials provided on, or incorporated into, the nasal mask and the oral appliance respectively.

The magnetic elements or materials may comprise neodymium magnets.

The ferromagnetic magnetic elements or materials may comprise magnetic and non-magnetic members.

The nasal mask may comprise a chin-engaging portion that comprises one or more ferromagnetic magnetic elements or materials that are attracted to one or more ferromagnetic magnetic elements or materials provided on, or incorporated into, the oral appliance.

The nasal mask may comprise:

a nose-engaging section; and a pair of face-engaging wing sections outwardly laterally extending away from the nose-engaging section in a pair of opposed directions.

The face-engaging wing sections may comprise a pair of arms adapted to engage left and right buccal regions of the user.

The arms may be dimensioned to conform with respective shapes of the buccal regions.

A pair of the ferromagnetic members may be positioned toward respective outermost ends of the arms.

A pair of the ferromagnetic magnetic elements or materials may be positioned toward respective outermost ends of the arms.

A pair of the ferromagnetic magnetic elements or materials may be positioned on respective opposed sides of the nose-engaging section.

A pair of the ferromagnetic magnetic elements or materials may be positioned on the chin-engaging portion.

The oral appliance may comprise uppermost and lowermost splints that engage with maxillary and mandibular teeth of the user respectively, wherein the splints are held in relative position by one or more supports extending between the splints to provide for mandibular advancement.

The supports of the oral appliance may be configured to hold the lowermost of the splints in a fixed position relative to the uppermost of the splints to provide the mandibular advancement.

The nose-engaging section may comprise a lowermost portion that defines a chamber underneath a pair of nostrils of the user when the user is wearing the mask, wherein the chamber is dimensioned to form an airtight seal about the nostrils. A hose may be connected to a lower end of the chamber, wherein the hose is configured to supply air upward from the hose into the chamber and such that the air flows upward through the chamber into the nostrils.

The present invention also provides a registration instrument for recording an anatomical bite registration for a person, wherein the instrument comprises:

a body having an outwardly extending rod at an end of the body, wherein the rod is configured to be inserted between maxillary and mandibular teeth of an oral cavity of the person and to be engaged by the teeth;

a marker comprising a first end and a second end, wherein the first end is adapted to be retained by a bite registration material when the bite registration material has cured inside the oral cavity to form a dental impression therein, and wherein the second end is dimensioned to protrude outwardly from the dental impression; and a connection mechanism that releasably connects the marker to the instrument, wherein the connection mechanism is adapted to allow the marker to stay retained within the dental impression when the rod is withdrawn from the dental impression.

The marker may be bifurcated such that its first end comprises a fork.

The connection mechanism may comprise a loop, wherein the loop is provided at the second end of the marker, and a channel provided in the body that receives the loop releasably.

The loop may be U-shaped or rectangular shaped.

The body may comprise a recess proximal to the channel that is adapted to receive a lever for releasing the loop from the channel.

The present invention also provides a process for manufacturing a breathing assistance apparatus, wherein the process comprises:

scanning an oral cavity of a person to generate oral geometric data;

scanning a face of the person to generate facial geometric data;

fabricating an oral appliance based on the oral geometric data, wherein the oral appliance comprises at least an uppermost splint adapted to engage with a set of maxillary teeth of the person;

fabricating a strapless positive airway pressure nasal mask based on the facial geometric data; and attaching or incorporating ferromagnetic magnetic elements or materials to, or into, each of the oral appliance and nasal mask, wherein one or more of the ferromagnetic magnetic elements or materials is or are magnetic such that the nasal mask and oral appliance are attracted to each other when the apparatus is being worn by the user.

The process for manufacturing the breathing assistance apparatus may include scanning maxillary and mandibular teeth of the oral cavity so that the oral geometric data includes maxillary and mandibular geometric data, and the oral appliance may be fabricated to include a lowermost splint adapted to engage with the mandibular teeth.

The process for manufacturing the breathing assistance apparatus may include adjusting a relative position of the uppermost and lowermost splints by a titration protocol to provide for mandibular advancement.

The titration protocol may include:

attaching one or more sensors to the person, wherein the sensors are adapted to generate data relating to breathing behaviour of the person;

collecting the data by the sensors when the user is sleeping; and adjusting a position of the lowermost of the splints relative to the uppermost of the splints based on the data to determine the mandibular advancement.

The process for manufacturing the breathing assistance apparatus may include:

performing the titration protocol, wherein the titration protocol includes determining a naturally occurring vertical opening between the maxillary and mandibular teeth of the person, and wherein the titration protocol includes determining an optimal position of mandibular antero-posterior, lateral and rotational planes relative to the maxillary teeth;

inserting the rod of the registration instrument into the oral cavity of the person and requiring the person to bite the rod, wherein the rod has a diameter corresponding to the naturally occurring vertical opening to stabilise a bite position of the person;

orientating the registration instrument relative to lips of the person so that the second end of the marker outwardly protrudes from the lips when the lips are passively sealed;

injecting a bite registration material into the oral cavity;

allowing the bite registration material to cure such that the bite registration material forms a dental impression of the maxillary and mandibular teeth and such that the first end of the marker is retained by the dental impression;

removing the dental impression from the oral cavity;

detaching the marker from the registration instrument;

removing the rod of the registration instrument from the dental impression such that the marker remains in the dental impression;

reinserting the dental impression and marker back into the oral cavity;

scanning the face of the person when the dental impression is being held by the teeth of the person to generate a set of facial geometric data, wherein the set of facial geometric data includes geometric data of the face and geometric data of the second end of the marker outwardly protruding from the lips of the person;

generating a first 3D computer model based on the set of facial geometric data, wherein the second end of the marker in the first 3D computer model provides a first pair of reference landmarks in 3D space;

removing the dental impression and marker from the oral cavity and scanning the dental impression and marker to generate a set of impression geometric data;

generating a second 3D computer model based on the set of impression geometric data, wherein the second end of the marker in the second 3D computer model provides a second pair of reference landmarks in 3D space;

generating a third 3D computer model based on the maxillary geometric data;

generating a fourth 3D computer model based on the mandibular geometric data:

using the second pair of reference landmarks to position and align the fourth 3D computer model relative to the third 3D computer model to produce a first aligned 3D computer model of the teeth of the person;

using the first pair of reference landmarks to position and align the first aligned 3D computer model relative to the first 3D computer model to produce a second aligned 3D computer model of the teeth of the person that accords with the mandibular advancement; and fabricating the oral appliance in accordance with the second aligned 3D computer model of the teeth.

The oral appliance and the nasal mask may each be fabricated using an additive manufacturing process.

The oral appliance may be fabricated using a sacrificial mold-based process.

The process for manufacturing the breathing assistance apparatus may include scanning mid and lower third facial regions of the face, including bridge, buccal and philtrum regions of the face, to produce the facial geometric data.

The present invention also provides a breathing assistance apparatus comprising a positive airway pressure nasal mask, wherein the nasal mask comprises:

a nose-engaging section that comprises a lowermost portion that defines a chamber underneath a pair of nostrils of a person wearing the mask, wherein the chamber is dimensioned to form an airtight seal about the nostrils; and a hose connected to a lower end of the chamber, wherein the hose is configured to supply air upwardly into the chamber such that the air flows upwardly through the chamber into the nostrils.

BRIEF DESCRIPTION OF DRAWINGS

Embodiments of the invention will now be described by way of example only with reference to the accompanying drawings, in which.

DESCRIPTION OF EMBODIMENTS

Figure 1:
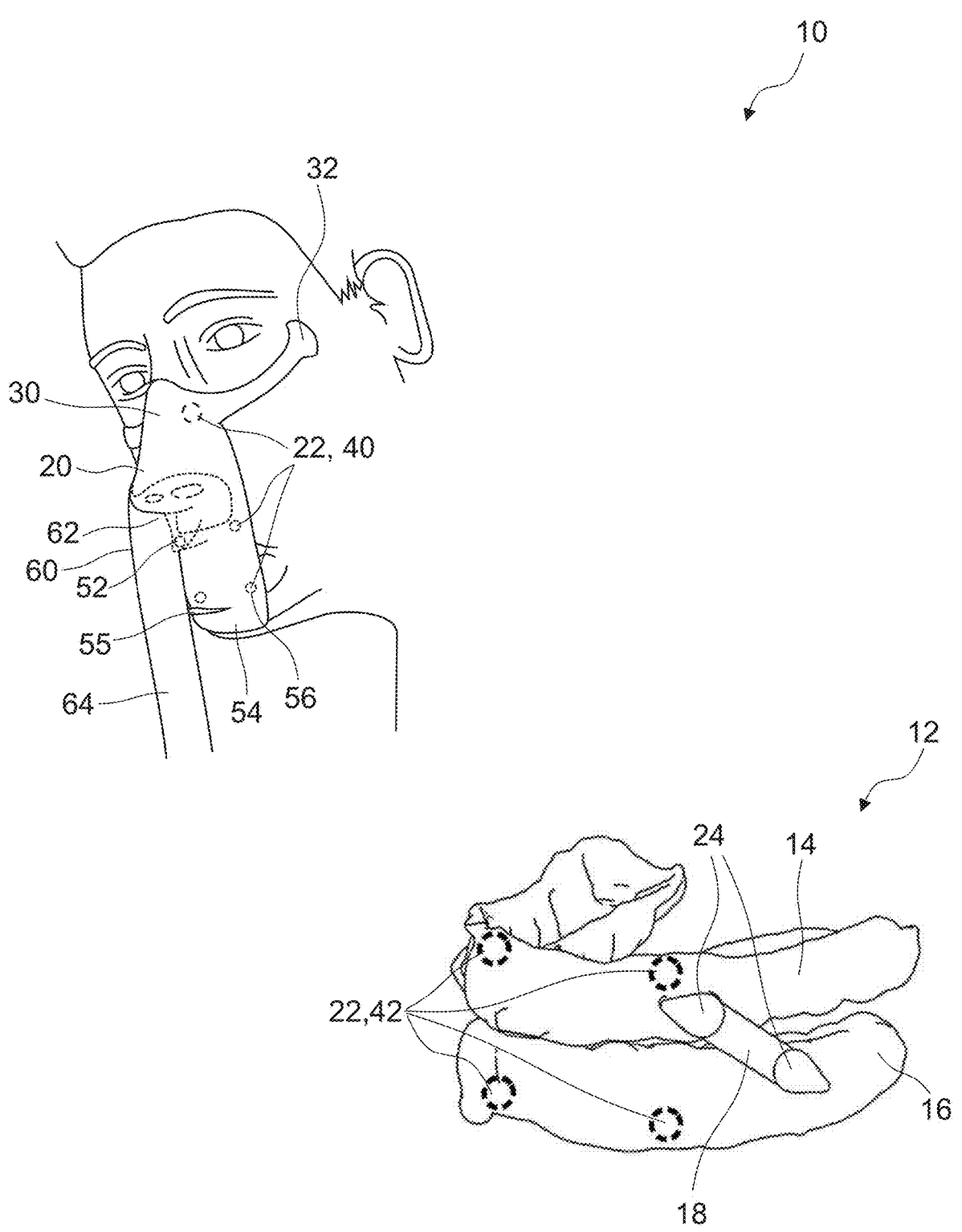
FIG. 1 shows a breathing assistance apparatus according to an example embodiment of the invention.

Referring to the FIGS. 1 to 5, an example embodiment of the present invention provides a breathing assistance apparatus 10. The apparatus 10 comprises an oral appliance 12 that has at least an uppermost splint 14 that is adapted to engage with a set of maxillary teeth. The apparatus 10 also comprises a strapless positive airway pressure nasal mask 20 and a plurality of ferromagnetic elements or materials 22 provided on the oral appliance 12 and nasal mask 20. The ferromagnetic elements or materials 22 comprise one or more magnets such that the nasal mask 20 and oral appliance 12 are attracted to each other when the apparatus 10 is being worn by a user.

Figure 2A:
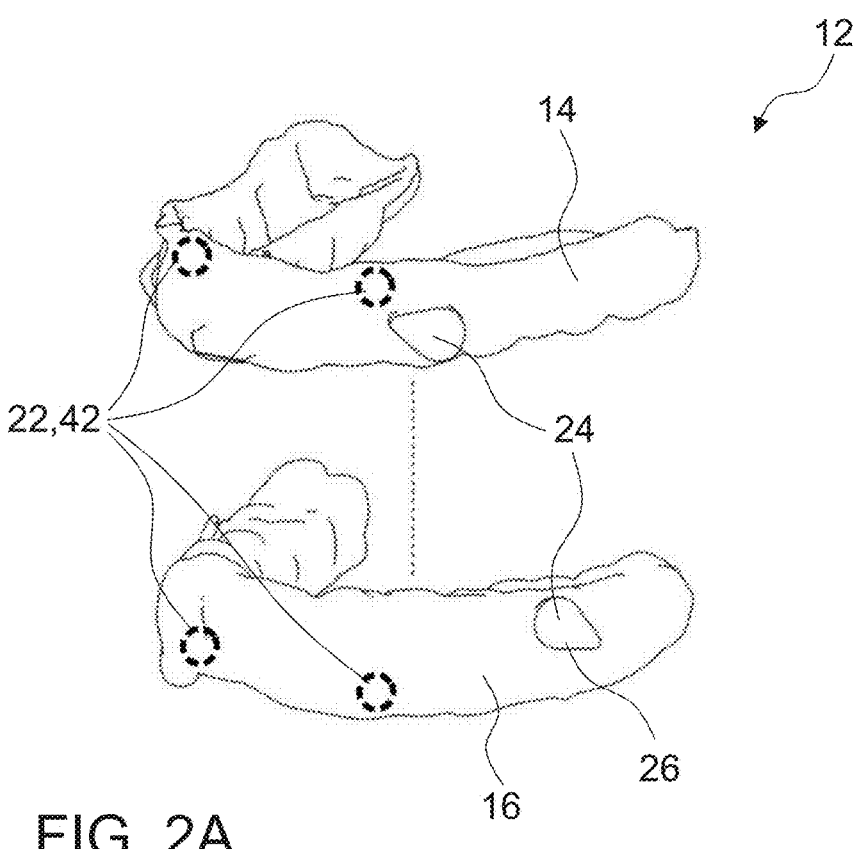
FIG. 2A is an exploded isometric view of an oral appliance of the apparatus.
Figure 2B:
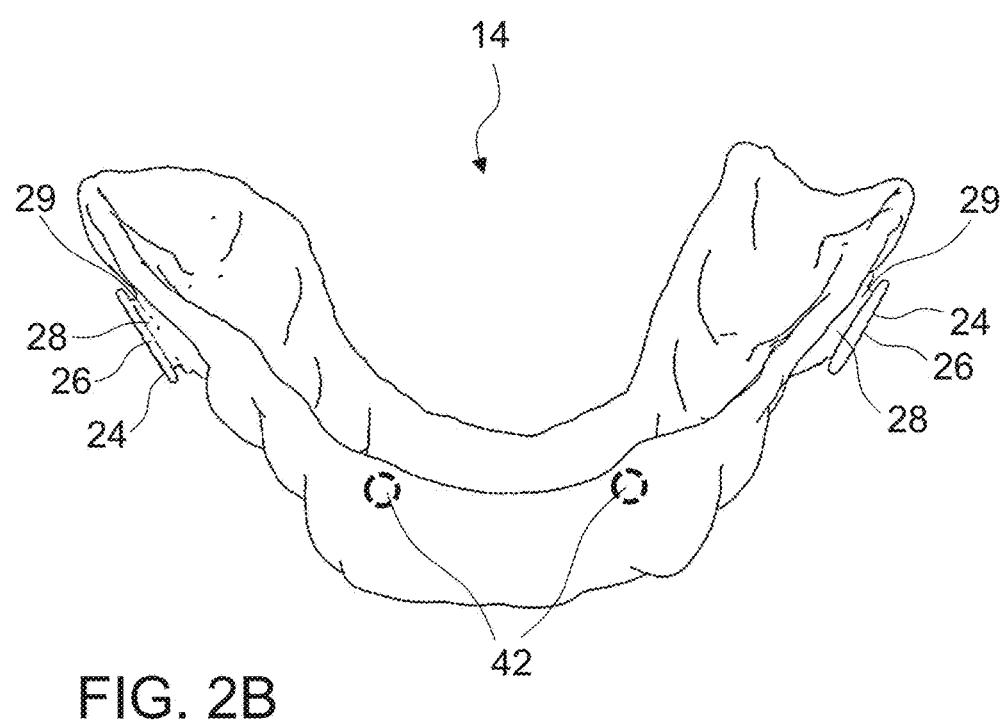
FIG. 2B is an isometric view of an uppermost splint of the oral appliance.

More particularly, referring to FIGS. 2A and 2B, in the example depicted the oral appliance 12 comprises an uppermost splint 14 and a lowermost splint 16. The uppermost splint 14 may be adapted to engage with, and receive, a set of maxillary teeth of the user. The lowermost splint 16 may, accordingly, be adapted to engage with, and receive, a set of mandibular teeth of the user. The two splints 14, 16 may be held in relative position by one or more supports 18 (see FIG. 1) extending between the splints 14, 16 to provide for mandibular advancement. Each splint 14, 16 may comprise a pair of fasteners 24 that are provided on respective opposed sides of the splint. Each individual fastener 24 may comprise a teardrop-shaped button 26 that is held spaced apart from the relevant splint by an outwardly-protruding spigot 28. The button 26 and spigot 28 of each fastener 24 may be shaped such that, as most clearly shown in FIG. 2B, a channel 29 is formed between the button 26 and spigot 28 that extends circumferentially around the spigot 28. The outermost longitudinal ends of each elongate support 18 may be adapted such that they are engageable into, and around, the channel 29 of a fastener 24 by a push or snap-fit arrangement.

The oral appliance 12 may comprise a pair of the supports 18 that engage with, respectively, opposed uppermost and lowermost of the fasteners 24 on each side of the oral appliance 12. The supports 18 may be substantially rigid such that the lowermost splint 16 is held in a fixed position relative to the uppermost splint 14. Preferably, the rigid supports 18 are oriented and dimensioned such that the lowermost splint 16 provides for efficacious mandibular advancement for the user when the oral appliance 12 is being worn. In other examples, elasticated bands may be used as the supports 18, instead of rigid members, that engage around the channels 29 of the fasteners 24. The teardrop shaped buttons 26 keep the bands secured in the channels 29 during use.

The apparatus 10 may be custom fabricated for the user using a manufacturing process that uses 3D scanning and additive manufacturing technologies. For example, the manufacturing process may include the steps of: (i) scanning an oral cavity of the user to generate oral geometric data, which may include scanning the maxillary and mandibular teeth of the oral cavity; (ii) scanning a face of the user to generate facial geometric data, which may include scanning the bridge, buccal and philtrum regions of the user's face; (iii) performing an additive manufacturing process (e.g., 3D printing) to fabricate the uppermost and lowermost splints 14, 16 of the oral appliance 12 based on the oral geometric data; (iv) connecting the uppermost and lowermost splints 14, 16 together using supports 18 to provide for mandibular advancement; and (v) performing an additive manufacturing process to fabricate the nasal mask 20 based on the facial geometric data. A similar manufacturing process may be performed to fabricate examples that have an oral appliance 12 with an uppermost splint 14 only. Once the nasal mask 20 and oral appliance 12 are formed, the ferromagnetic members 22 may then be secured to the mask 20 and oral appliance 12 in the relevant positions using an appropriate attachment means. For example, the ferromagnetic members 22 may be secured in position using adhesive, clip arrangements or by interference fit within prefabricated cavities formed in the respective parts of the apparatus 10.

In other examples, the oral appliance 12 and/or mask 20 may be custom fabricated using manufacturing techniques other than additive manufacturing. For example, the oral appliance 12 may be produced by a sacrificial mold injection process.

The process of validating and fine tuning the relative splint positions to achieve the maximal anatomic airway opening for the user of the oral appliance 12, and thus clinical efficacy, may be further assisted by following a titration protocol. For example, the titration protocol may involve obtaining quantitative sleep data for the user and adjusting the relative splint positions based on the data over a series of test iterations. At the start of the protocol, the supports 18 may be attached to the splints 14, 16 such that the lowermost splint 16 is set at an initial position relative to the uppermost splint 14. The initial length and/or orientation of each support 18 that achieves the initial position may be determined from digital records obtained from maxillary and mandibular scans. Orientated phonetic bite registration records, as discussed below, may also be used to determine the initial position.

Once the lowermost splint 16 has been set in position, the oral appliance 12 may then be provided to the user for testing. To test the appliance 12, the user may wear the oral appliance 12 overnight and data relating to their breathing behaviour may be collected while they are sleeping. Based on these data, the advancement of the lowermost splint 16 relative to the uppermost splint 14 may be adjusted in an effort to improve the user's breathing. The adjustments may be made by removing the two supports 18 and replacing them with ones having different shapes and/or lengths. The adjusted oral appliance 12 may then be provided back to the user for further testing and data collection.

The testing and adjustment process may be repeated for multiple iterations until a suitable mandibular advancement for the user has been achieved. In one example, one or more sensors may be attached to the user (for example, to one of their fingers) to collect snoring/breathing data on an automatic basis during each test iteration. The sensors may comprise, for example, one or more (i) audio sensors for collecting snoring and/or breathing noise data, (ii) air flow or pressure sensors for collecting inhalation and exhalation breathing data, (iii) oxygen level and/or heart rate sensors. The data collected may be stored on a digital storage device provided on the sensors, or may be transmitted to a remote device or platform (including a cloud-based platform) for subsequent analysis by, for example, a wireless communication means.

In other examples, the appropriate relative splint positions for the user may be determined by recording a bite registration, or interocclusal record, for the user using an anatomical registration protocol. A variety of registration protocols known in the dental profession may be used. For example, the protocol that is commonly known as the "phonetic bite" process may be followed. This process involves the use of a handheld instrument having a rounded rod at its end that is placed between the user's teeth to stabilise their achieved phonetic bite position. More particularly, the registration process may include the following steps: (i) asking the user to occlude their teeth a number of times to assess their natural occlusion; (ii) noting the dental and skeletal midlines of the user to note whether they coincide; (iii) observing the user's face in a mirror and asking them to count out a loud through a range of numbers and noting the numbers that result in the widest naturally occurring vertical opening between their maxillary and mandibular teeth respectively and for maximum anterior posterior positioning: (iv) selecting an instrument that has a rod with the requisite diameter that stabilises the user's achieved phonetic bite position when the user is biting the rod; (v) inserting the instrument into the user's mouth and asking them to bite the rod; (vi) while the user is biting the rod, injecting a rapid set bite registration material into the user's mouth such as, for example, a rubber or silicone-based registration material; (vii) allowing the registration material to cure; and (viii) removing the cured registration material and instrument from the user's mouth and then measuring and/or computer scanning the bite impressions left in the cured material by the user's teeth to determine the relative splint positions.

Referring now to FIGS. 17 to 20, there is depicted an improved instrument 100 for recording anatomical bite registrations. The instrument 100 may be used to fabricate the oral appliance 12 with relative splint positions that provide for efficacious mandibular advancement suitable for a user. The instrument comprises a body 102 having an outwardly extending rod 104 at an end of the body 102. The rod 104 is configured to be inserted between maxillary and mandibular teeth of an oral cavity of the person and to be engaged by the teeth. The instrument 100 also comprises a marker 106 comprising a first end 108 and a second end 110. The first end 108 is adapted to be retained by a bite registration material when the bite registration material has cured inside the person's oral cavity to form a dental impression therein. The second end 110 is adapted to protrude outwardly from the dental impression. The instrument 100 also comprises a connection mechanism 112 for releasably connecting the marker 106 to the body 102 of the instrument 100. The connection mechanism 112 is adapted such that the marker 106 remains fixed in the dental impression when the rod 104 is withdrawn from the dental impression.

Figure 23:
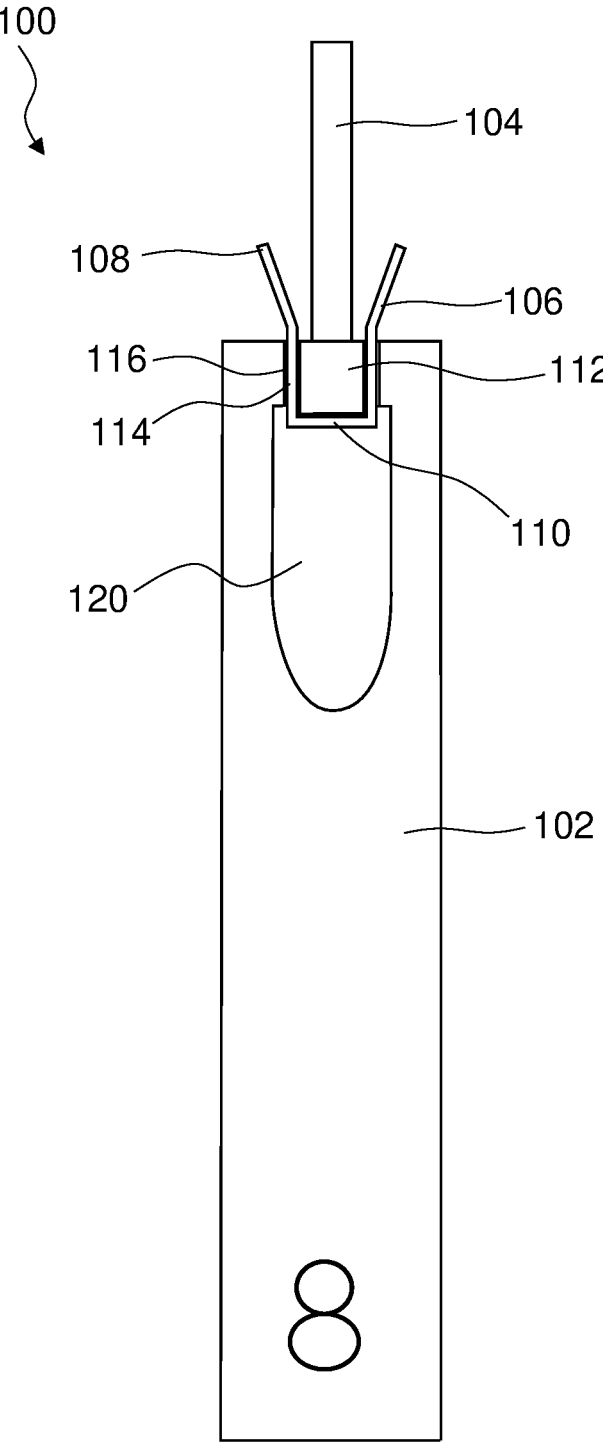
FIG. 23 is an isometric view of an instrument used to perform a bite registration process when manufacturing a breathing assistance apparatus in a further example embodiment of the invention.

More particularly, the marker 106 may be bifurcated such that its first end 108 comprises a fork and such that its second end 110 comprises a pair of marker portions that converge together to form a loop 114. The loop 114 may be adapted to engage releasably into a channel 116 provided on the body 102. The loop 114 and channel 116 may be dimensioned complementary to one another such that they together provide the releasable connection mechanism 112. In the example depicted in FIGS. 17 to 20, the loop 114 and the channel 116 are U-shaped. The body 102 may comprise a concave recess 120 proximal to the channel 116. The recess 120 is adapted to receive a lever, such as the end of a screwdriver or the user's finger or thumb, to allow the marker 106 to be disengaged from the channel 116. As shown in FIG. 23, in another example the loop 114 of the instrument 100 may be rectangular shaped, rather than U-shaped, and the channel 116 may accordingly be dimensioned to receive the rectangular loop 114.

Figure 21:
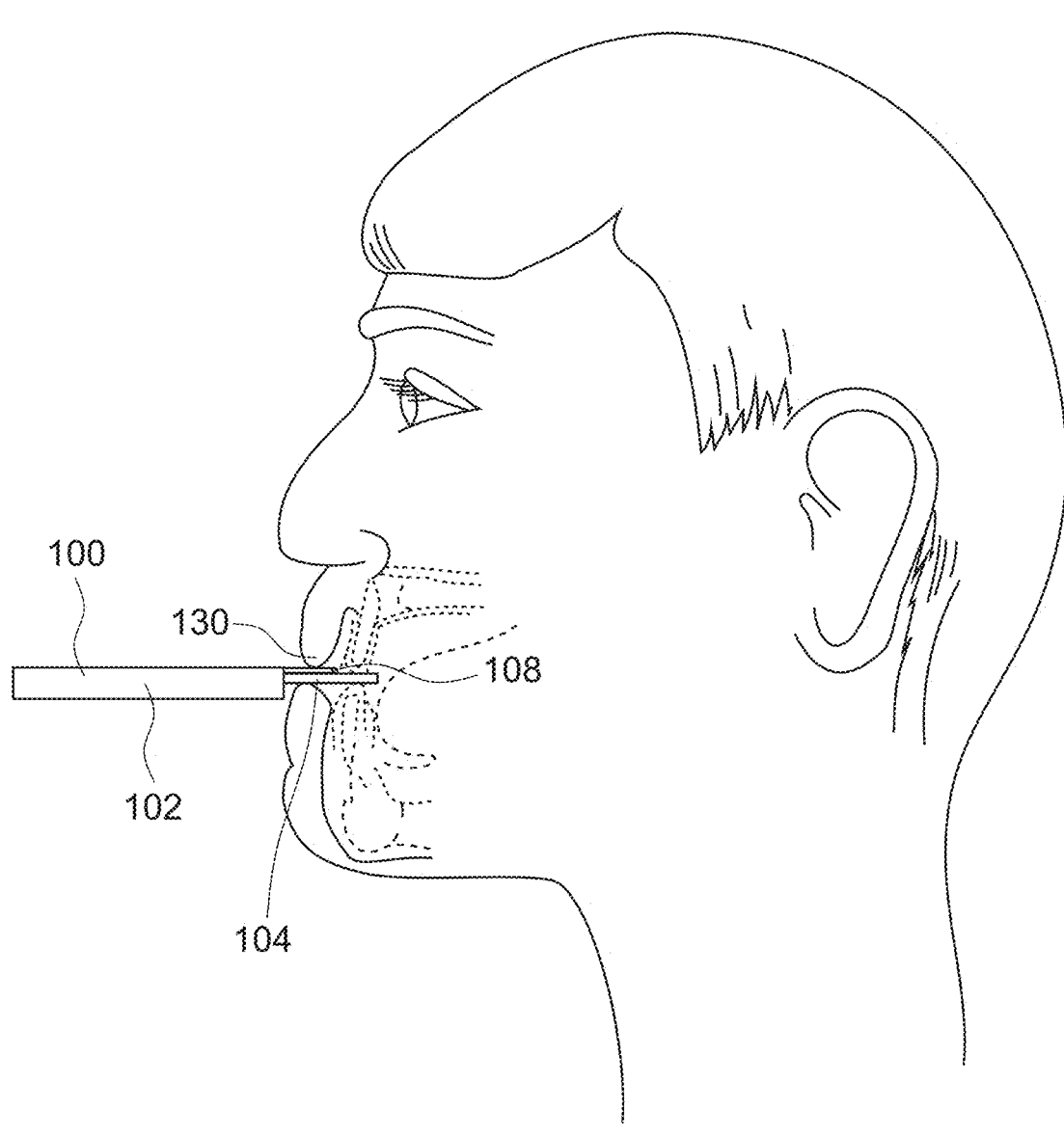
FIG. 21 is a side elevation view of a person's head with the registration instrument arranged in the person's mouth.

In use, the instrument 100 is suited for a range of bite registration protocols that may be followed when performing the manufacturing process for the apparatus 10, including the phonetic bite registration protocol discussed above. To obtain an effective bite registration for a person, a set of the instruments 100 will typically be available that have rods 104 with a range of different diameters. For example, a set of the instruments 100 may be provided having rod diameters within the range 3-8 millimeters (mm). For the first step in manufacturing a custom oral appliance 12 for the given person, the bite registration protocol will be followed to determine a suitable mandibular advancement for the person. For example, this protocol may involve (i) determining the naturally occurring vertical opening between the person's maxillary and mandibular teeth, and (ii) determining an optimal position of mandibular antero-posterior, lateral and rotational planes relative to their maxillary teeth. An instrument 100 will then be selected from the set that has a rod 104 with a diameter corresponding to the naturally occurring vertical opening to stabilise the person's bite position. The rod 104 will then be inserted into the person's mouth and the person will be asked to bite the rod, as illustrated in FIG. 21. The registration instrument 100 will then be oriented relative to the person's lips 130 so that the second end 110 of the marker 106 outwardly protrudes from the lips 130 when the lips 130 are passively sealed. A portion of curable bite registration material 132 will then be injected into the oral cavity and allowed to cure.

Figure 22:
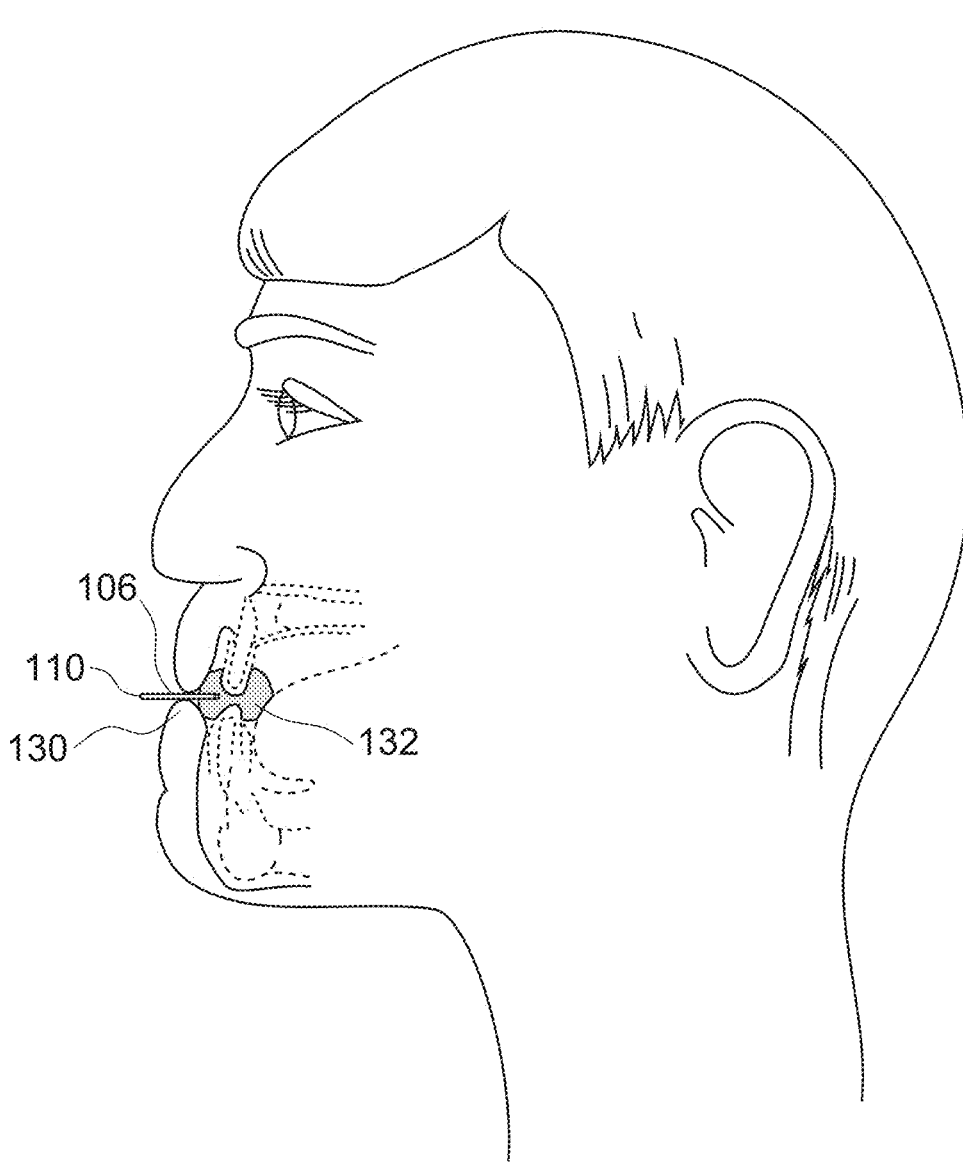
FIG. 22 is a side elevation view of the person shown in FIG. 21, wherein a portion of cured bite registration material is inside the person's mouth and the marker of the registration instrument is retained by the registration material.

As illustrated in FIG. 22, once cured the bite registration material forms a dental impression 132 of the person's maxillary and mandibular teeth in their mouth. The forked end 108 of the marker 106 is also retained within the cured dental impression 132 inside the mouth. The two peripheral ends of the fork 108 ensure that the end of the marker 106 is securely affixed within the dental impression 132. The dental impression 132 will then be removed from the person's mouth and the marker 106 will be detached from the registration instrument 100. The detachment may be achieved by placing a lever implement, such as a screwdriver end, into the recess 120 and using the implement to prise the second marker end 110 upwards and away from the body 102. The rod 104 will then be extracted from the dental impression 132 by pulling the body 102 away from the impression 132. If there is any excessive solidified impression material and/or excessive undercuts on the impression 132, then the relevant parts may be removed or trimmed away using a scalpel blade.

The dental impression 132 and marker 106 will then be reinserted back into the person's mouth to verify the fit and to ensure that the marker 106 outwardly projects through the person's lips when passively sealed, as shown in FIG. 22. While the impression 132 is being held clamped by the person's teeth (and thus holding their lower jaw in accordance with the bite registration record), the person's face will then be scanned to generate a set of facial geometric data. The set of facial geometric data will include geometric data of the face and geometric data of the looped portion 114 of the marker 106 outwardly protruding from the person's lips 130. A first 3D computer model will then be generated based on the set of geometric data. The looped end 114 of the marker 106 in the first 3D computer model provides a first pair of identifiable reference landmarks in 3D space. That is to say, the two elongated parts of the second marker end 110 that form the loop 114 (being the parts labeled 115a and 115b in FIG. 19) provide the two respective landmarks.

The dental impression 132 will then be removed once again from the person's mouth. The impression 132 and marker 106 will then be scanned to generate a set of impression geometric data. A second 3D computer model will then be generated based on the impression geometric data. The looped second end 110 of the marker 106 in the second 3D computer model provides a second pair of reference landmarks in 3D space. A third and a fourth 3D computer model will then be generated based on, respectively, the maxillary and mandibular geometric data previously obtained during the manufacturing process.

The second pair of reference landmarks can then be used to position and align the fourth 3D computer model relative to the third 3D computer model. This alignment process, which may be done using suitable 3D modelling computer software, results in the production of a first aligned 3D computer model of the person's teeth. The first pair of reference landmarks in the first 3D computer model will then be used to position and align the first aligned 3D computer model relative to the first 3D computer model. This results in the production of a second aligned 3D computer model. The second aligned 3D computer model provides an accurate (and final) 3D model of the person's teeth that accords with the required mandibular advancement for the subject person. The oral appliance 14 can then be fabricated in accordance with the final 3D model. The final 3D model can also be used to select the positions of the ferromagnetic members 22 disposed on the mask 20 and oral appliance 12.

The instrument 100 can be used in a similar manner to register and align any anatomic portion(s) of the surface of the person's face with intra-oral records during manufacture of the apparatus 10. Further, whilst the instrument 100 has been described in the context of its use for bite registration protocols, it will be appreciated that the novel arrangement and configuration of the body 102 and detachable marker 106 may also be used in protocols used to obtain registrations of other anatomical features.

For certain users, the oral appliance 12 of the apparatus 10 may not necessarily need to provide for mandibular advancement. The oral appliance 12 may, therefore, only comprise the uppermost splint 14. For example, if the relevant user does not suffer from severe OSA, then only a PAP mask may be prescribed for them rather than the combination PAP mask 20 and oral appliance 12 with mandibular advancement splint 16 depicted in FIG. 1. In such cases, the lowermost splint 16 may be dispensed with and the uppermost splint 14 serves only to provide a convenient support for the oral-based ferromagnetic members 22 to be attached to.

Figure 3:
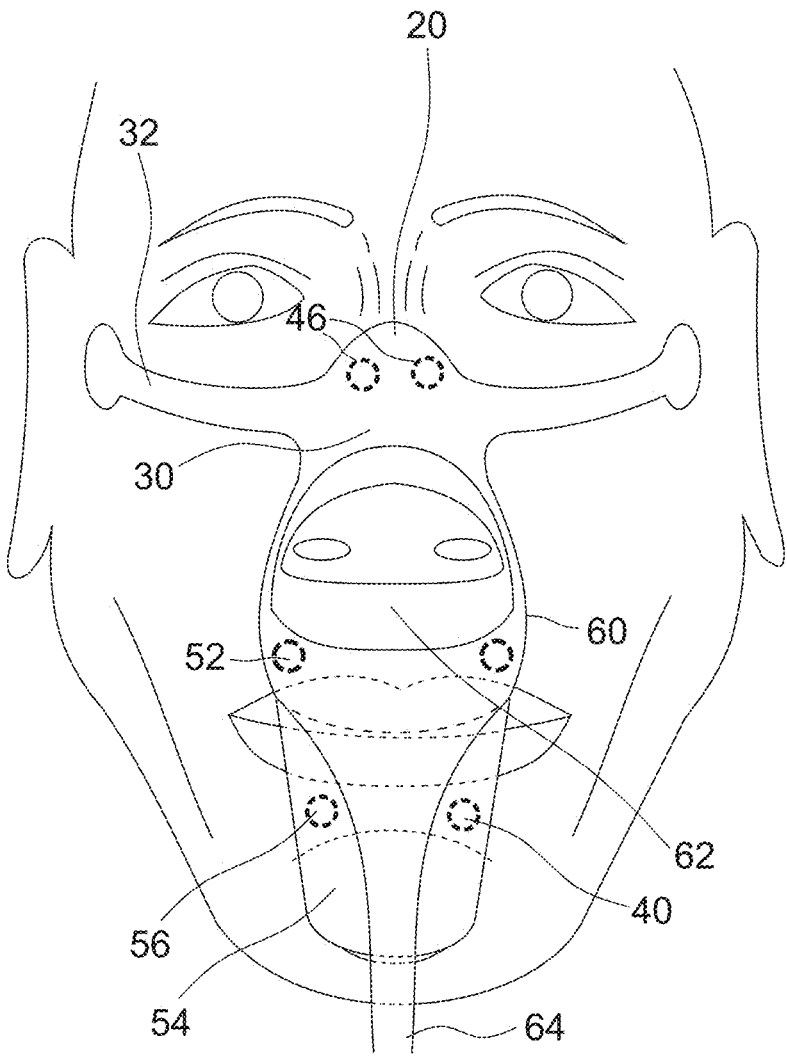
FIG. 3 is a front elevation view of a nasal mask of the apparatus shown partially in cross section.
Figure 4:
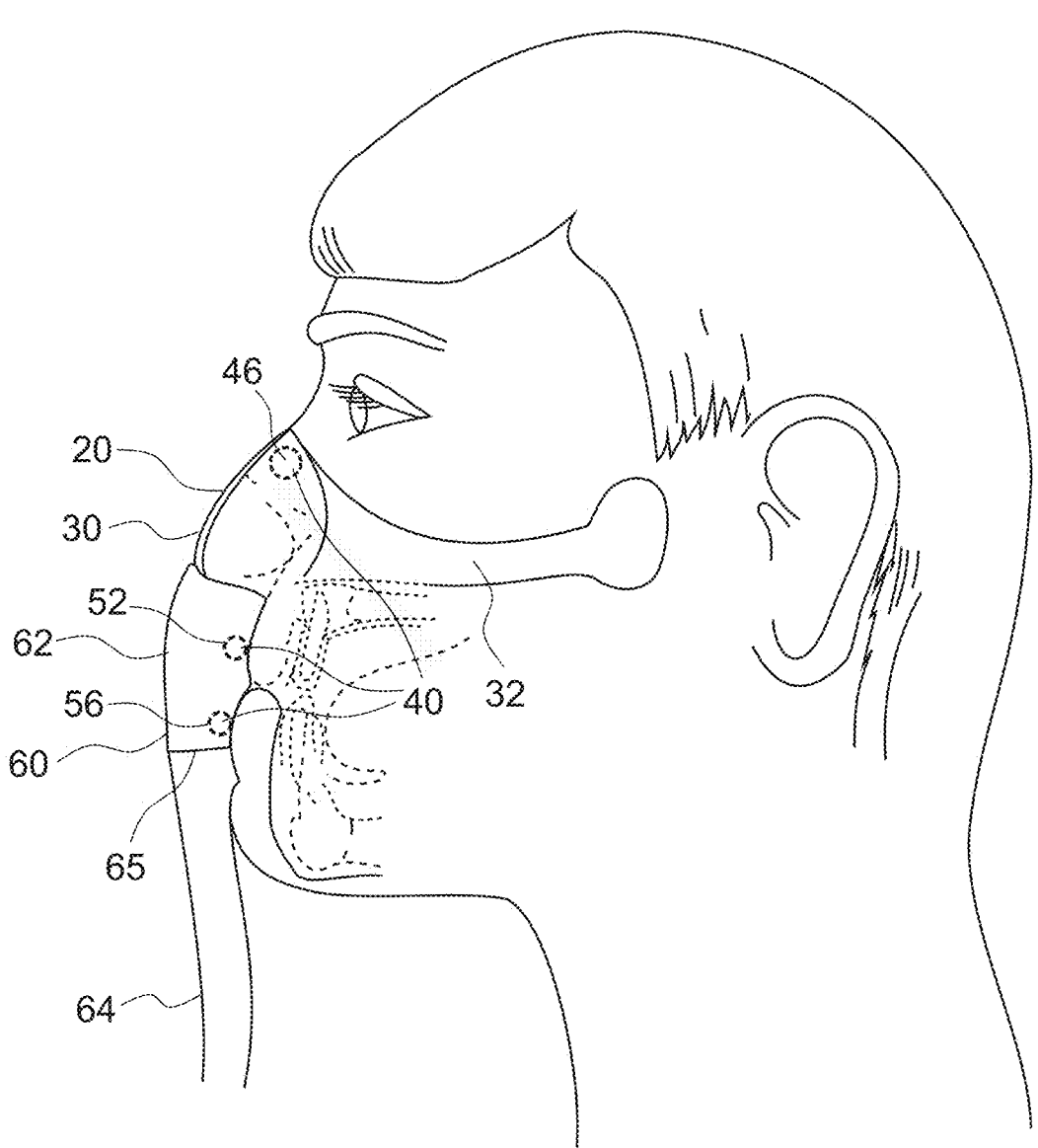
FIG. 4 is a side elevation view of the nasal mask.

Referring to FIGS. 3 and 4, the nasal mask 20 may comprise a nose-engaging section 30 and a pair of face-engaging wing sections 32 that outwardly laterally extend away from the nose-engaging section 30 in a pair of opposed directions. The face-engaging wing sections 32 may comprise a pair of arms that are adapted to engage left and right buccal regions of the user's face respectively. The arms 32 may be custom fabricated for the user of the apparatus 10 during the manufacturing of the apparatus 10 such that the arms 32 conform with the shapes of the buccal regions of the user's face. In this configuration, the arms 32 extend across the buccal regions such that the arms 32 are substantially in abutting contact with the buccal regions. The nose-engaging section 30 may also be customised for the user such that it conforms with the shape of the user's nose. In this configuration, the nose-engaging section 30 is closely fitted to the nose such that it extends over the bridge of the nose and is held in abutting contact with the bridge and the sides of the nose. In some examples, the user's facial geometry may allow the mask 20 to be held in a stable position without the arms 32. The arms 32 may, therefore, not be added to the mask 20 during the manufacturing process.

The ferromagnetic members 22 may comprise a first set of magnets 40 that are provided on the nasal mask 20 and a second set of magnets 42 that are provided on the oral appliance 12. The two sets of magnets 40, 42 may be relatively arranged such that opposed magnetic poles of the magnets 40, 42 are attracted to one another between the nasal mask 20 and the oral appliance 12. The magnetic fields of the magnets 40, 42 will be sufficiently strong such that the magnets 40, 42 influence each other between the nasal mask 20 and the oral appliance 12. In one example, the magnets 40, 42 may comprise neodymium magnets. Each of the magnets in the first set 40 may be paired with a corresponding individual magnet in the second set 42, such that each of the relevant pairs are attracted to each other.

In other examples, the ferromagnetic members 22 may comprise both magnetic and non-magnetic members. For example, the first set of members 40 provided on the nasal mask 20 may comprise neodymium magnets and the second set of members 42 on the oral appliance 12 may comprise non-magnetic members made of metal that are attracted to the neodymium magnets 40. In another example, the second set of members 42 on the oral appliance 12 may be magnetic and the first set of members 40 on the nasal mask 20 may comprise non-magnetic metal members.

In other examples, the ferromagnetic members 22 of the apparatus 10 may comprise a single ferromagnetic member on the nasal mask 20 and a single ferromagnetic member on the oral appliance 12, wherein at least one of the two ferromagnetic members is magnetic. For example, the oral appliance 12 may comprise a metal plate (not shown) embedded into an undersurface of the uppermost splint 14. The mask 20 may comprise a shaped magnetic plate (also not shown) embedded in, or attached to, a surface of the nose-engaging section 30 of the mask 20 that conforms to the shape of the surface.

Figure 5:
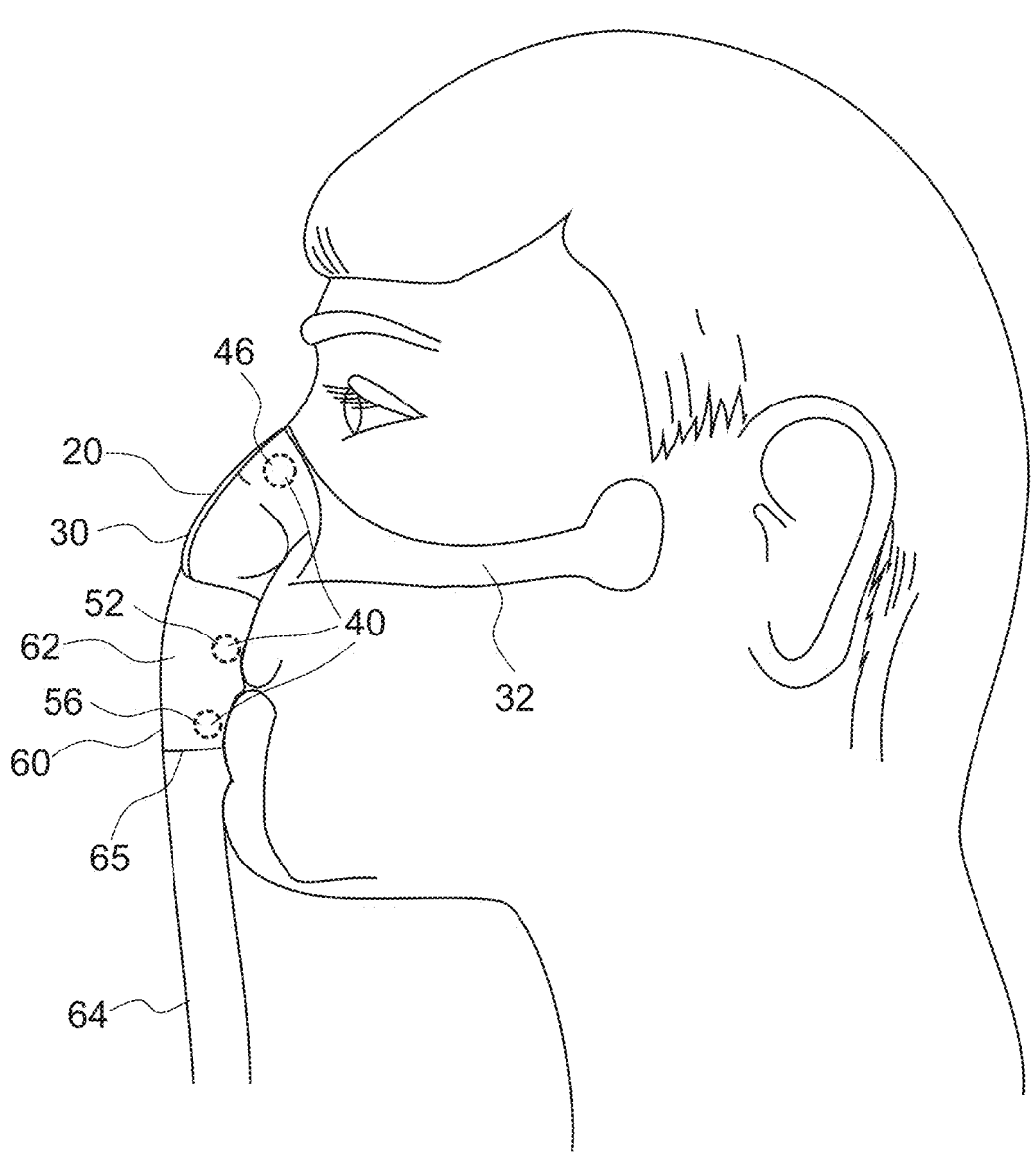
FIG. 5 is a further side elevation view of the nasal mask.
Figure 6:
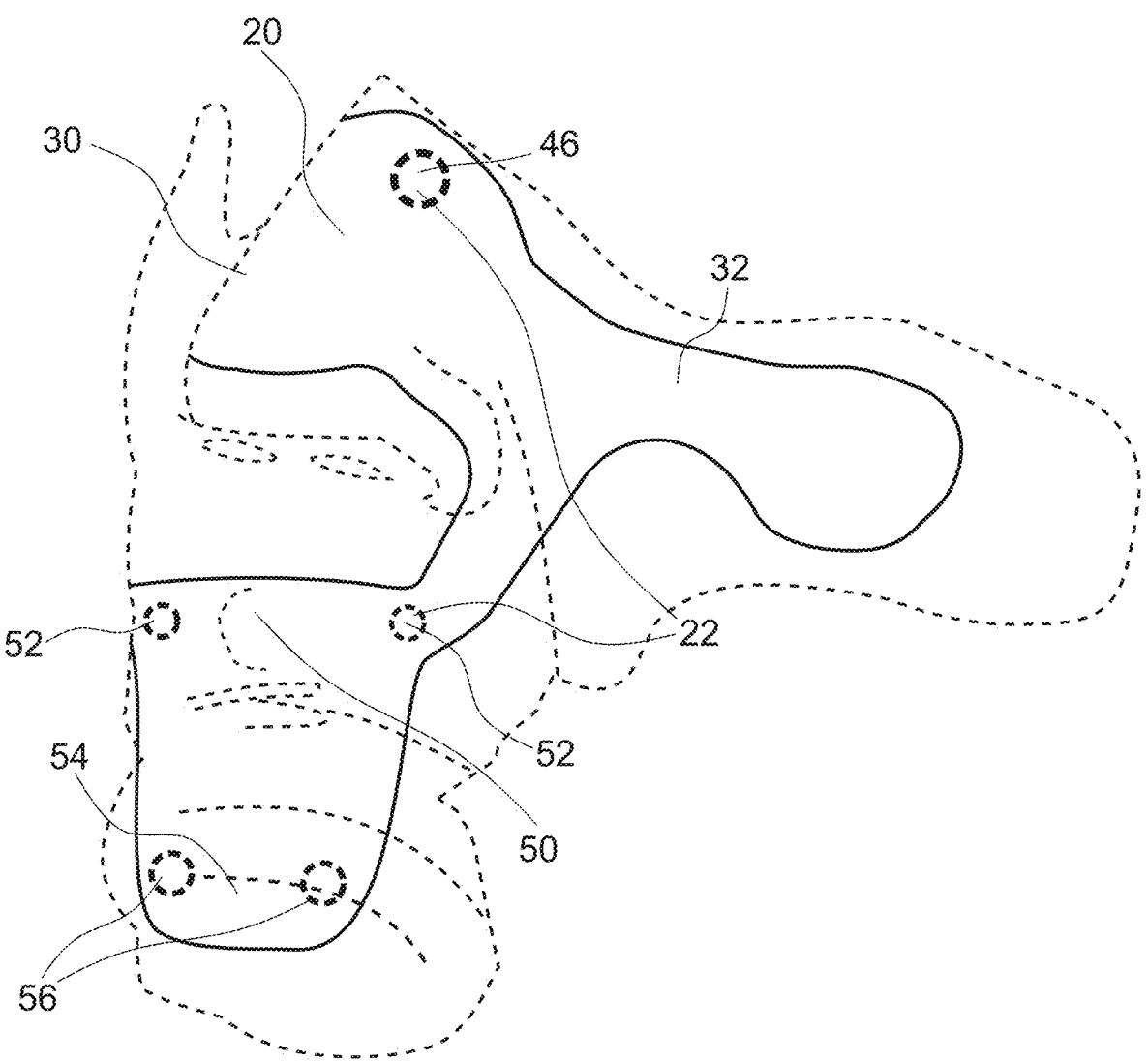
FIG. 6 is a schematic isometric view illustrating a footprint region of a person's face engaged by a nasal mask of a breathing assistance apparatus according to a further example embodiment of the invention.

Referring to FIGS. 3 to 5, the ferromagnetic members 22 on the mask 20 may comprise a set of small ferromagnetic buttons that are attached to, or embedded into, the mask 20 at various positions. A pair of the buttons 46 may be positioned on respective opposed sides of the nose-engaging section 30 of the mask 20. FIG. 6 shows the footprint region of a person's face that may be engaged by the nasal mask 20 in another example. The nasal mask 20 may comprise a philtrum-engaging region 50 that extends downwardly from the arms 32 and the nose-engaging section 30 of the mask 20. The region 50 may be dimensioned to extend laterally across the philtrum of the user and bear against the philtrum. The philtrum-engaging region 50 may comprise a pair 52 of the ferromagnetic buttons 22. The nasal mask 20 may also comprise a chin-engaging portion 54 extending continuously down from the philtrum-engaging region 50. The chin-engaging portion 54 may also comprise a pair of ferromagnetic buttons 56. The ferromagnetic buttons 52, 56 may each be attracted to one or more of the ferromagnetic members 42 provided on the oral appliance 14.

The chin-engaging portion 54 may be attached to a rearmost side of the hose 64 of the nasal mask 20 by an inwardly projecting connection member 55 (see FIG. 1). In other examples, the hose 64 may extend sufficiently close to the user's chin region such that the connection member 55 is not required, as shown in FIGS. 4 and 5. In other examples, the ferromagnetic members 22 of the mask 20 may be arranged at positions different to those depicted. For example, the ferromagnetic members 22 may be provided on just the chin-engaging portion 54.

Referring to FIGS. 1 and 3-5, the nose-engaging section 30 of the nasal mask 20 may comprise a lowermost portion 60 that defines a chamber 62 underneath a pair of nostrils of the user when the user is wearing the mask 20. The chamber 62 is dimensioned such that it forms an airtight seal about the nostrils of the user. A hose 64 may be connected to a lower end 65 of the chamber 62. The hose 64 may be configured such that it supplies compressed air upward from the hose 64 into the chamber 62, and such that the air flows in an upwards direction through the chamber 62 into the user's nostrils. The chamber 62 provides a cavity or void underneath the nostrils and the outlet end of the hose 64 that feeds into the chamber 62 is spaced apart from the nostrils. In this configuration, the chamber 62 advantageously allows the air flowing upward into the chamber 62 from the hose 64 to flow into the nostrils through the cavity in an identical flow path to natural inhalation/exhalation in a straight line configuration. The chamber 62 is below the nares and, therefore, advantageously encourages natural inhalation into the nose. The profile and configuration of the chamber 62 and hose 64 advantageously allows the direction of the path of the airflow to align with natural nasal breathing and accommodates natural variations in breathing through the nostrils.

Figure 7:
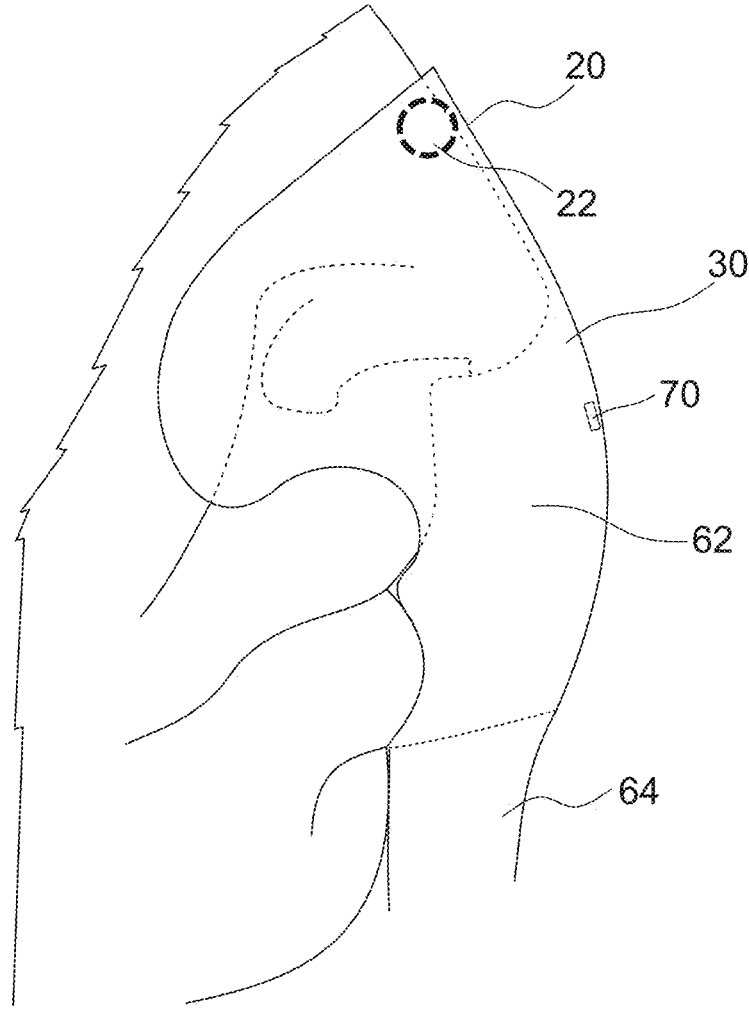
FIG. 7 is a side elevation view of a nose-engaging section of a nasal mask of a breathing assistance apparatus according to a further example embodiment of the invention.

Referring to FIG. 7, in other examples the chamber 62 may have one or more small exhalatory ports/vents 70 formed through its surface that operate to regulate air pressure and flow within the chamber 62. The ports/vents may be customised during manufacture of the apparatus 10 and be tailored to suit the user's anatomical and breathing requirements. It will be appreciated that the chamber 62 and hose 64 arrangement may equally be used with strap-based nasal PAP masks in addition to the strapless mask 20 herein disclosed. For example, a strapless mask 20 solution may not be suitable for a user that has a large beard or moustache. In such cases, elastic straps may be attached to the mask to the user's head in lieu of the ferromagnetic members 22.

Figure 8:
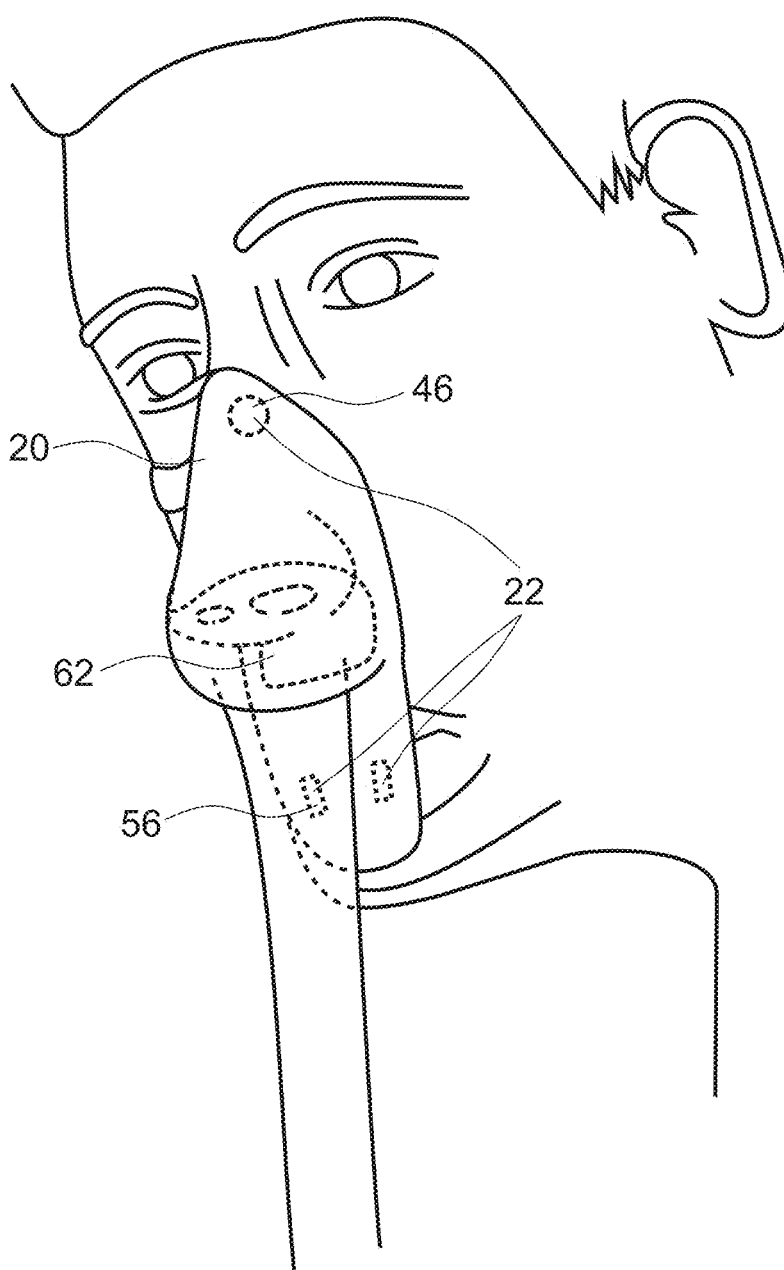
FIG. 8 is an isometric view of a nasal mask of a breathing assistance apparatus according to a further example embodiment of the invention.
Figure 9:
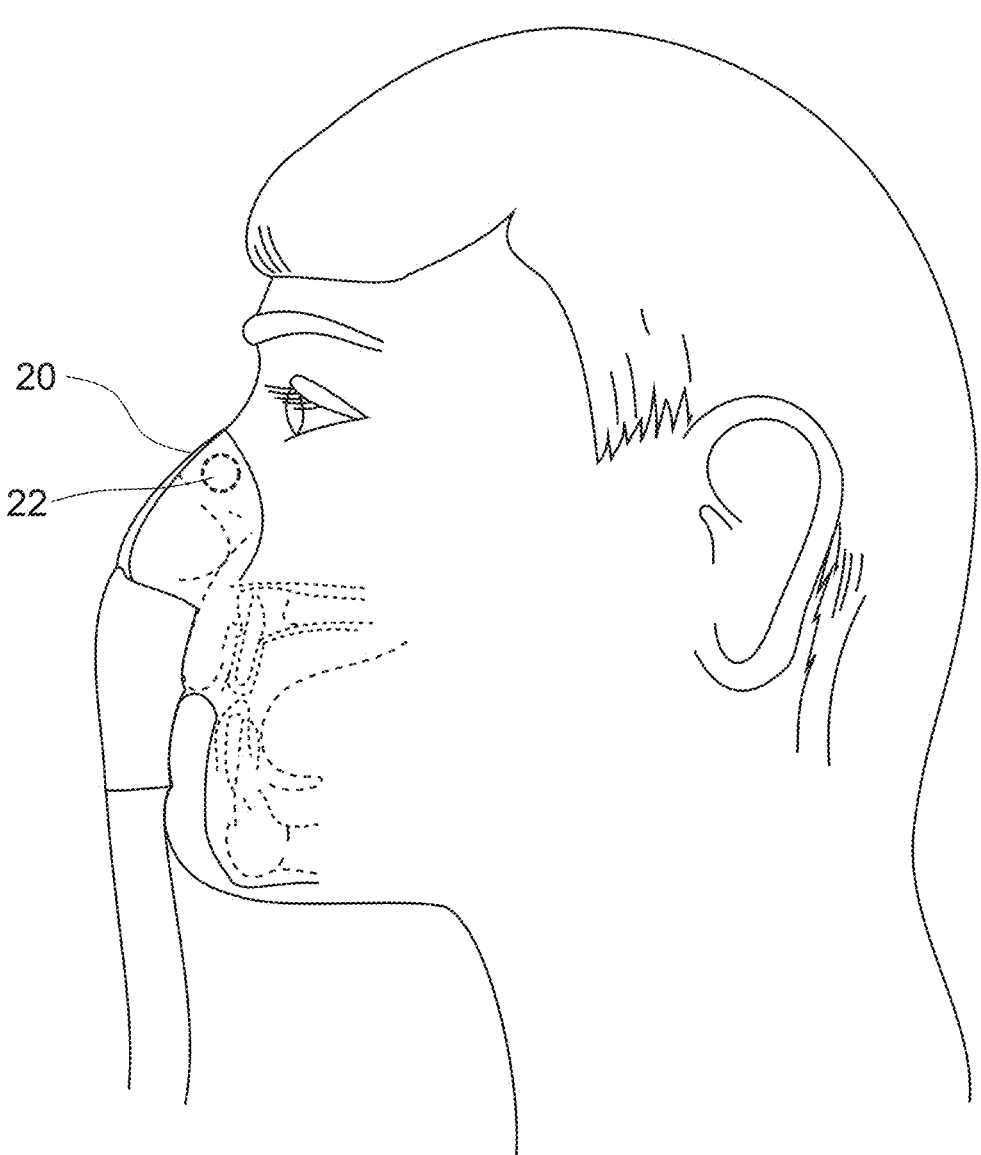
FIG. 9 is a side elevation view of the nasal mask of FIG. 8.
Figure 10:
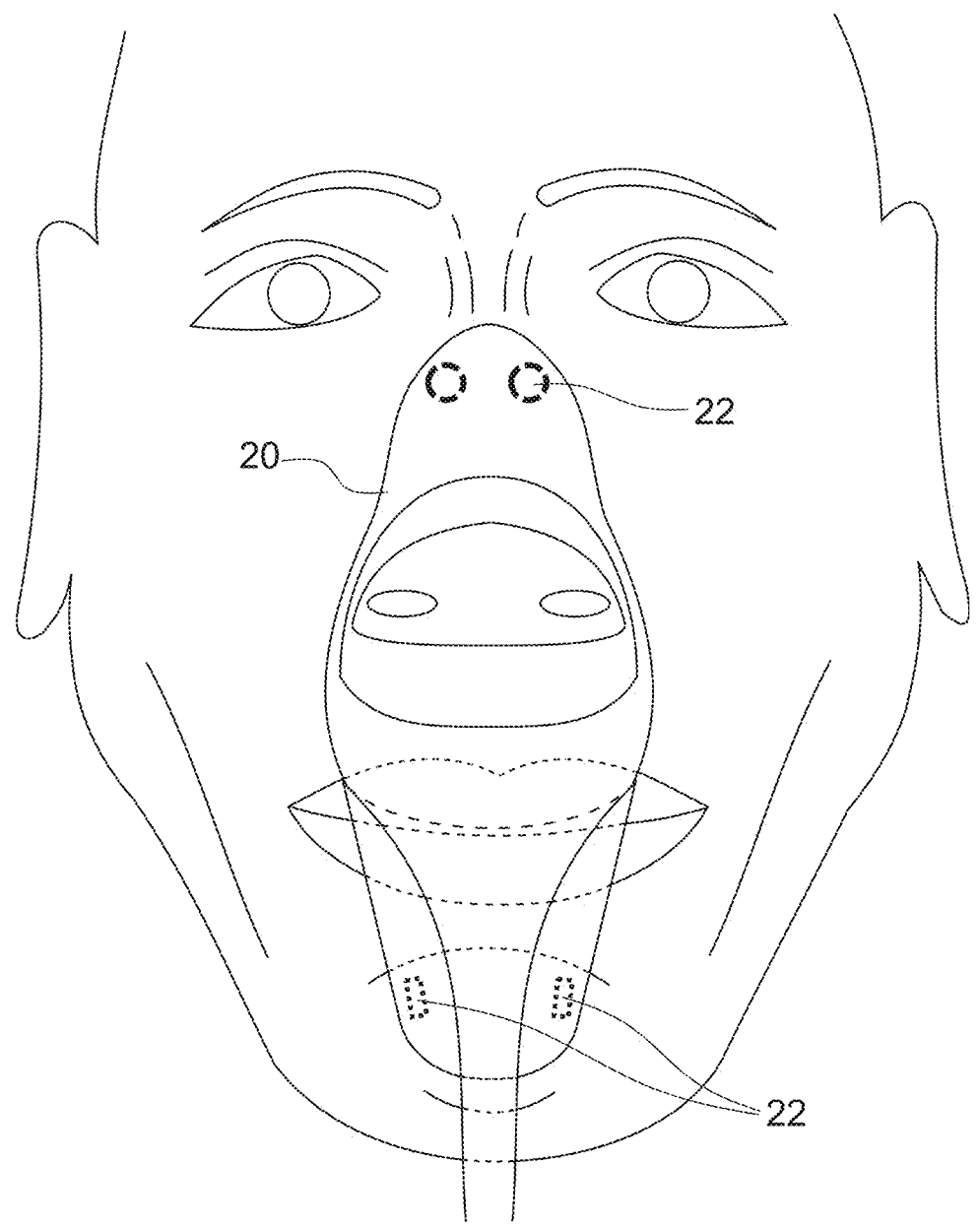
FIG. 10 is a front elevation view of the nasal mask of FIG. 8 shown partially in cross section.
Figure 11:
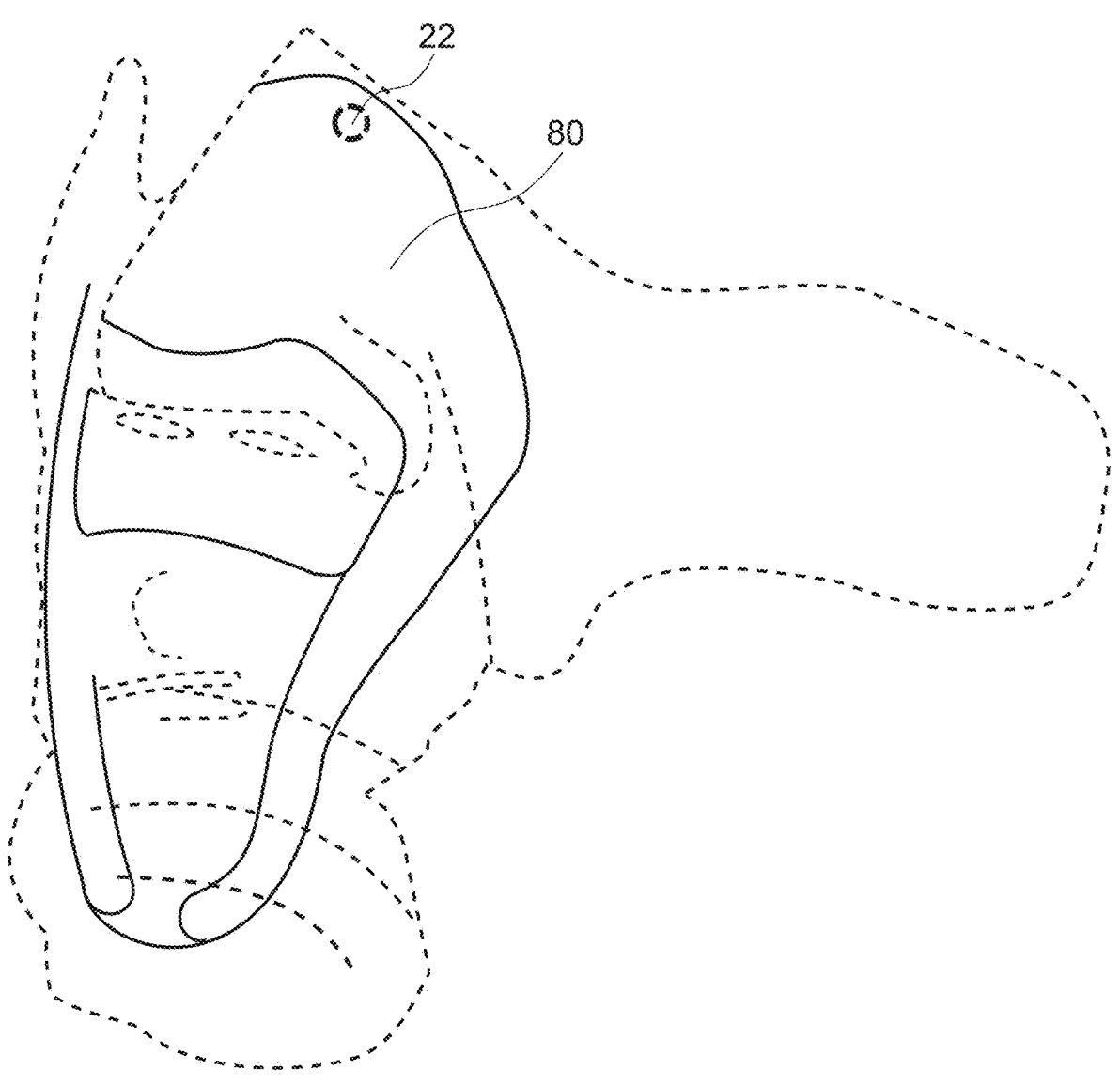
FIG. 11 is a schematic isometric view illustrating a footprint region of a person's face engaged by the nasal mask of FIG. 8.

FIGS. 8 to 10 illustrate an example of the nasal mask 20 that does not include arms 32. The region of the user's face that the mask 20 bears against during use is sufficiently large in surface area such that the mask 20 stays securely anchored to the face by the magnets 22 and stable during use. The facial footprint region 80 of a further example nasal mask not including arms 32 is shown in FIG. 11.

The nasal mask 20 may be fabricated in two portions that are joined together during manufacture of the apparatus 10. The first portion may bear against the surface of the user's face and form the nose-engaging section 30 of the mask 20. The second portion of the mask 20 may form the chamber 62 underneath the nostrils of the user that forms the airtight seal about the nostrils. The first and second mask portions may be joined together using suitable attachment means such as, for example, biomedical grade resin adhesive or by extruded-bead sealing or plastic welding.

Figure 12:
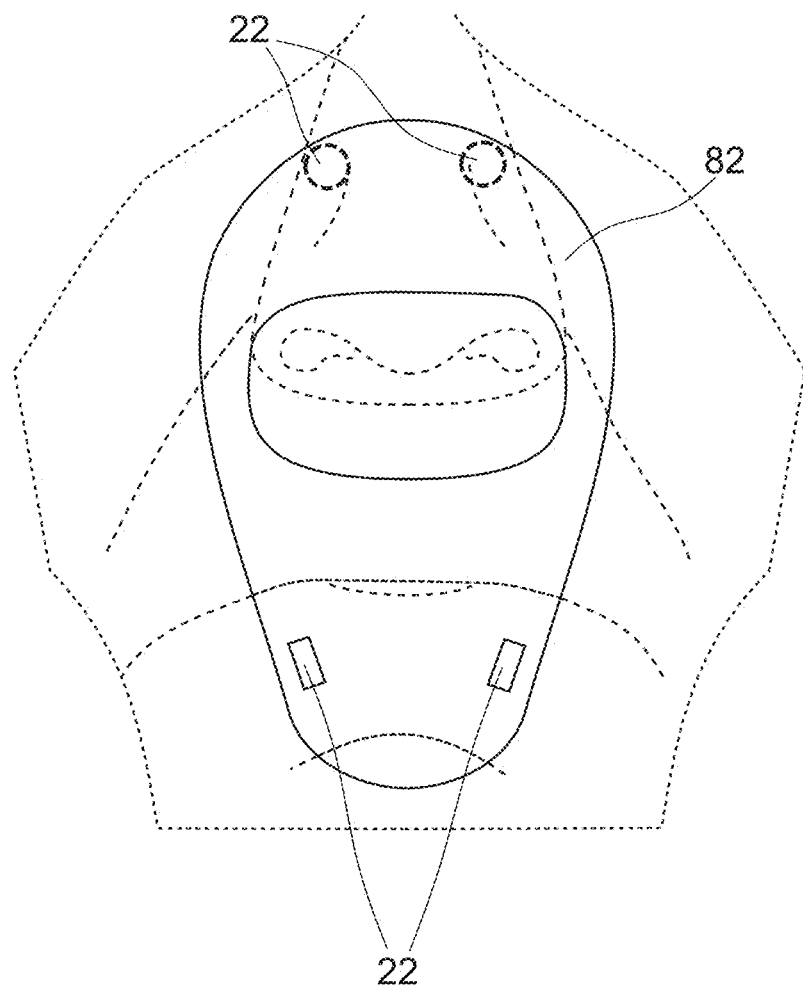
FIG. 12 is a front view of a face-engaging portion of a nasal mask of a breathing assistance apparatus according to a further example embodiment of the invention.
Figure 13:
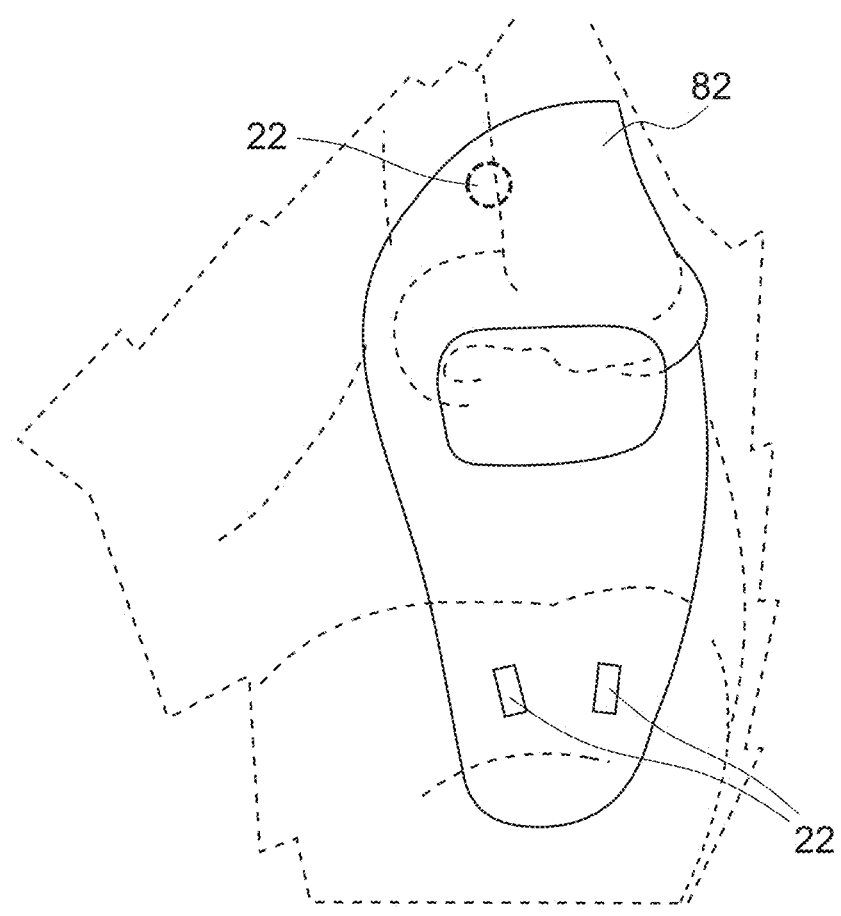
FIG. 13 is an isometric view of the face-engaging portion of the nasal mask of FIG. 12.
Figure 14:
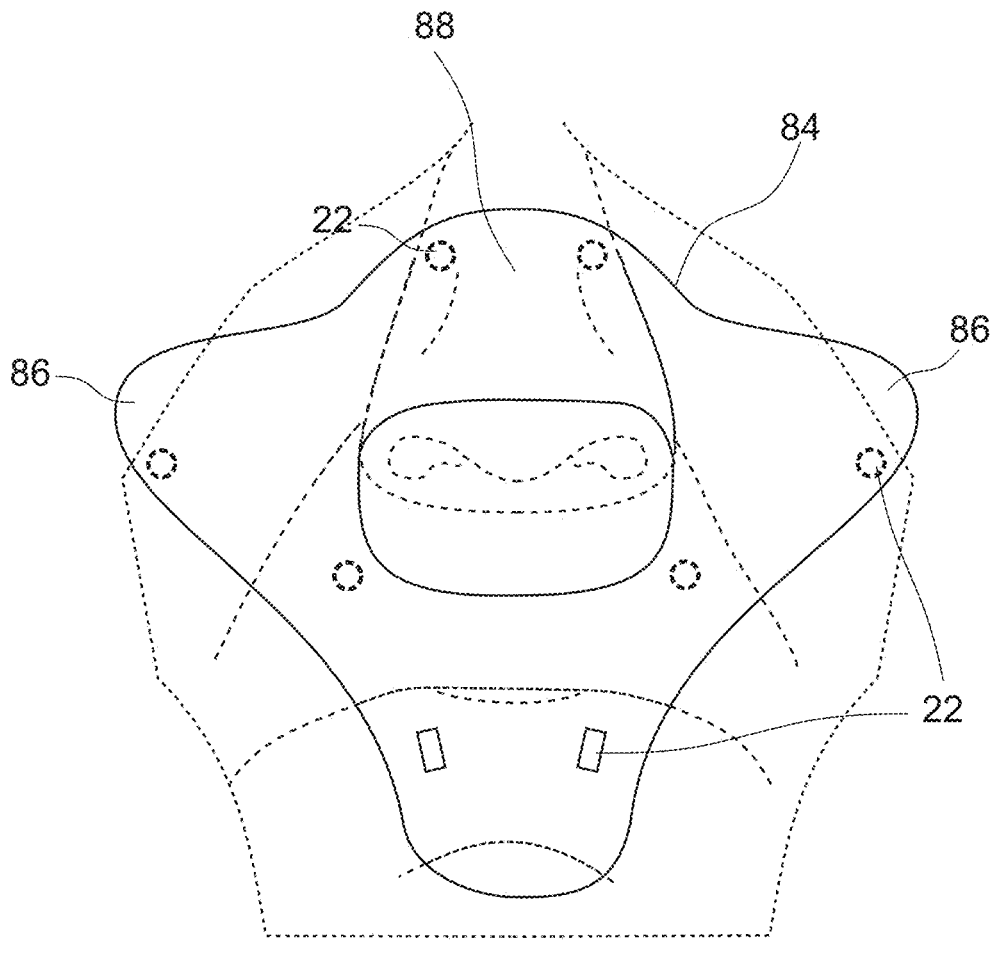
FIG. 14 is a front view of a face-engaging portion of a nasal mask of a breathing assistance apparatus according to a further example embodiment of the invention.
Figure 15:
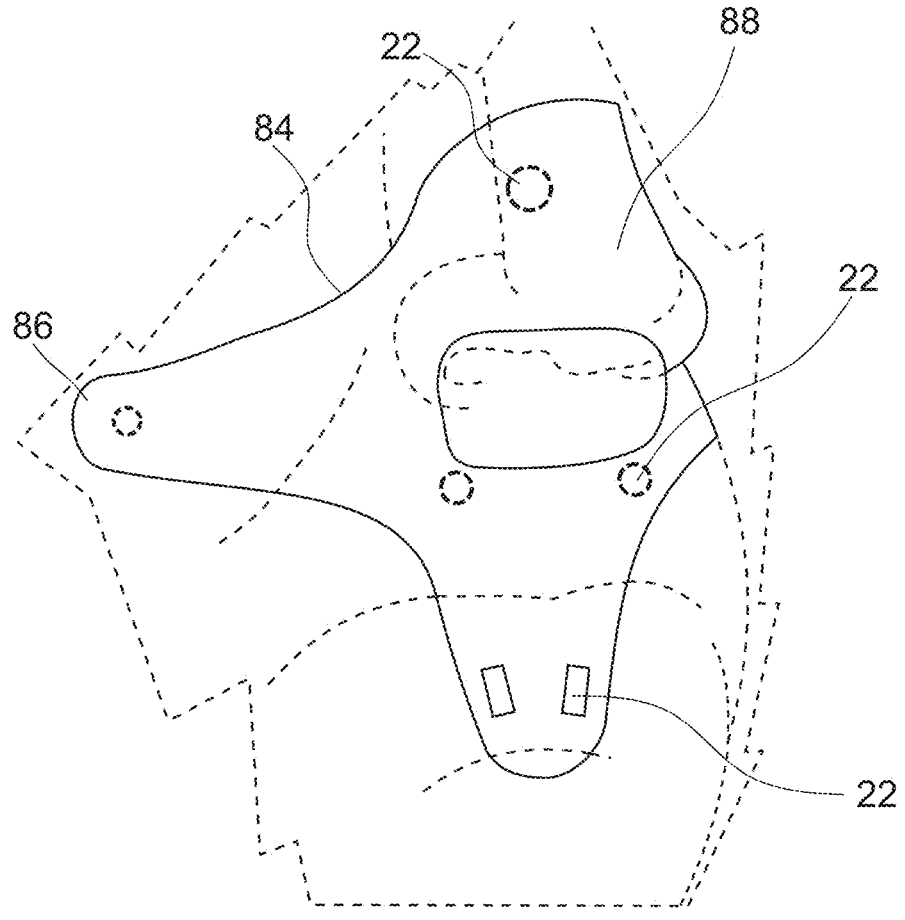
FIG. 15 is an isometric view of the face-engaging portion of the nasal mask of FIG. 14.
Figure 16:
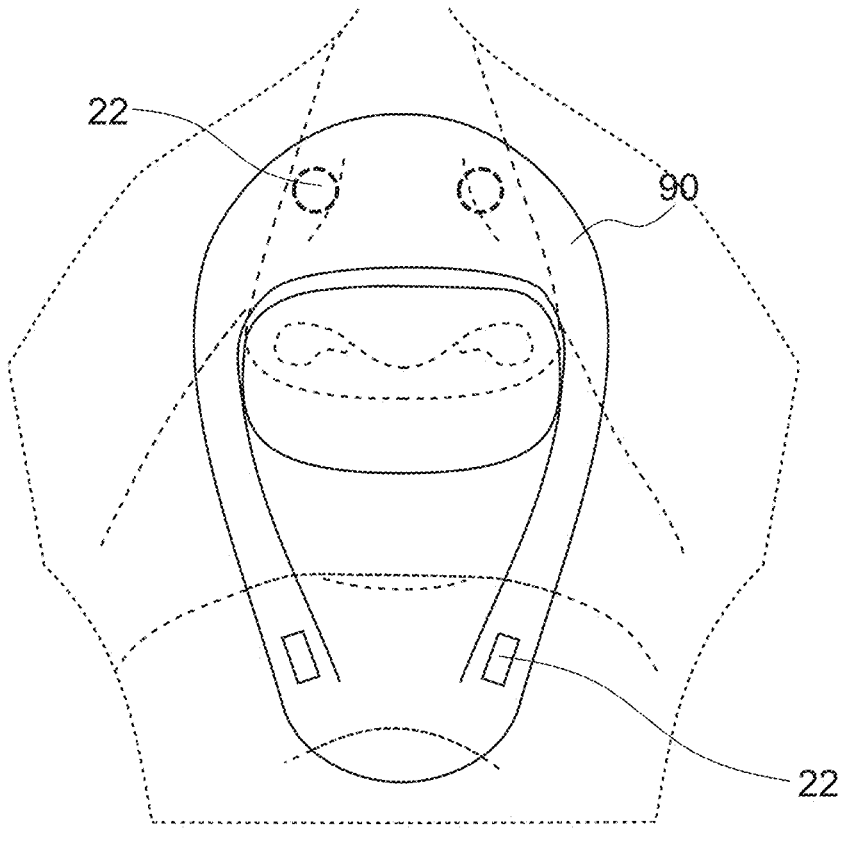
FIG. 16 is a front view of a face-engaging portion of a nasal mask of a breathing assistance apparatus according to a further example embodiment of the invention.
Figure 17:
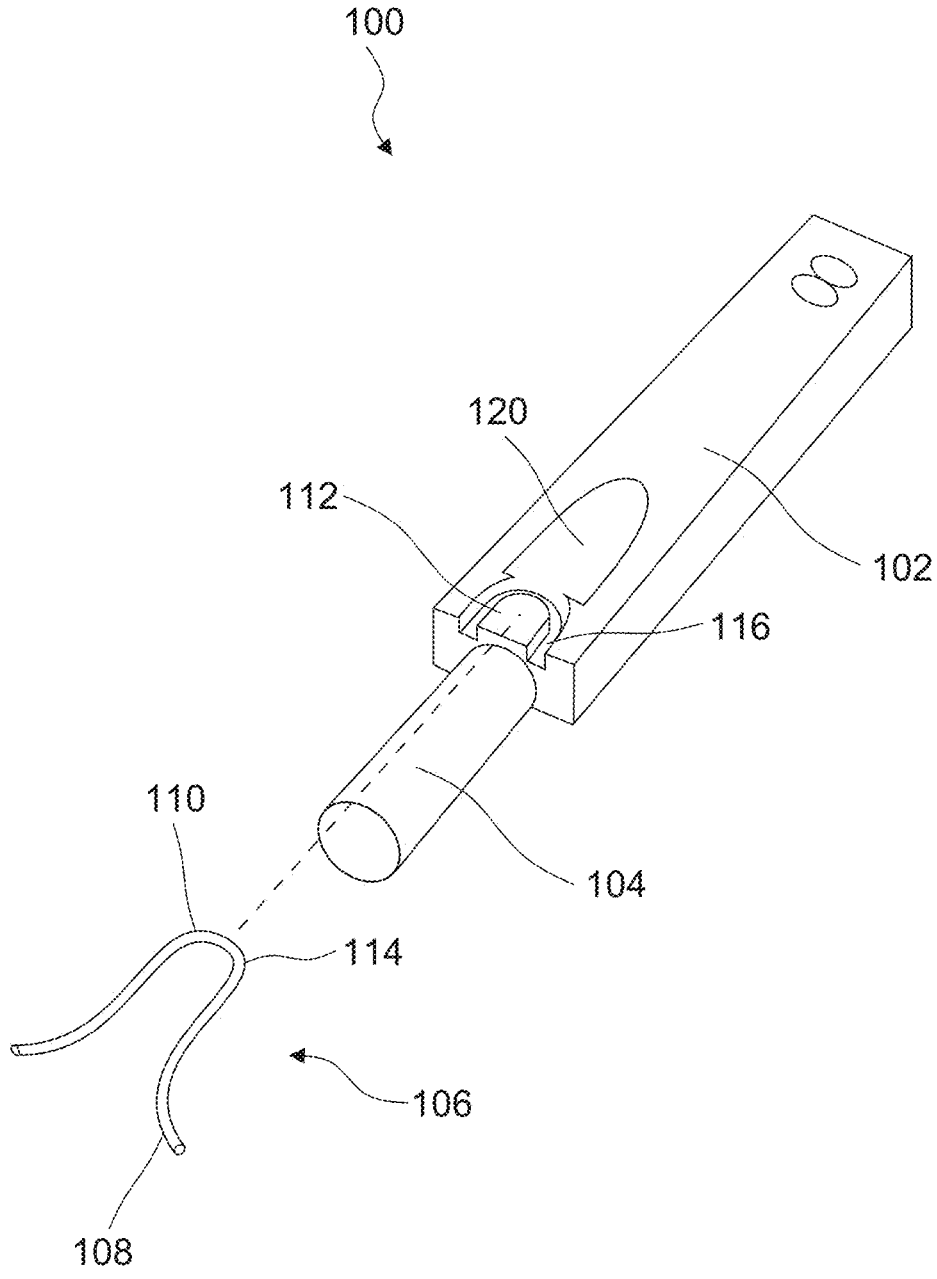
FIG. 17 is an exploded isometric view of an instrument used to perform a bite registration process when manufacturing a breathing assistance apparatus in a further example embodiment of the invention.
Figure 18:
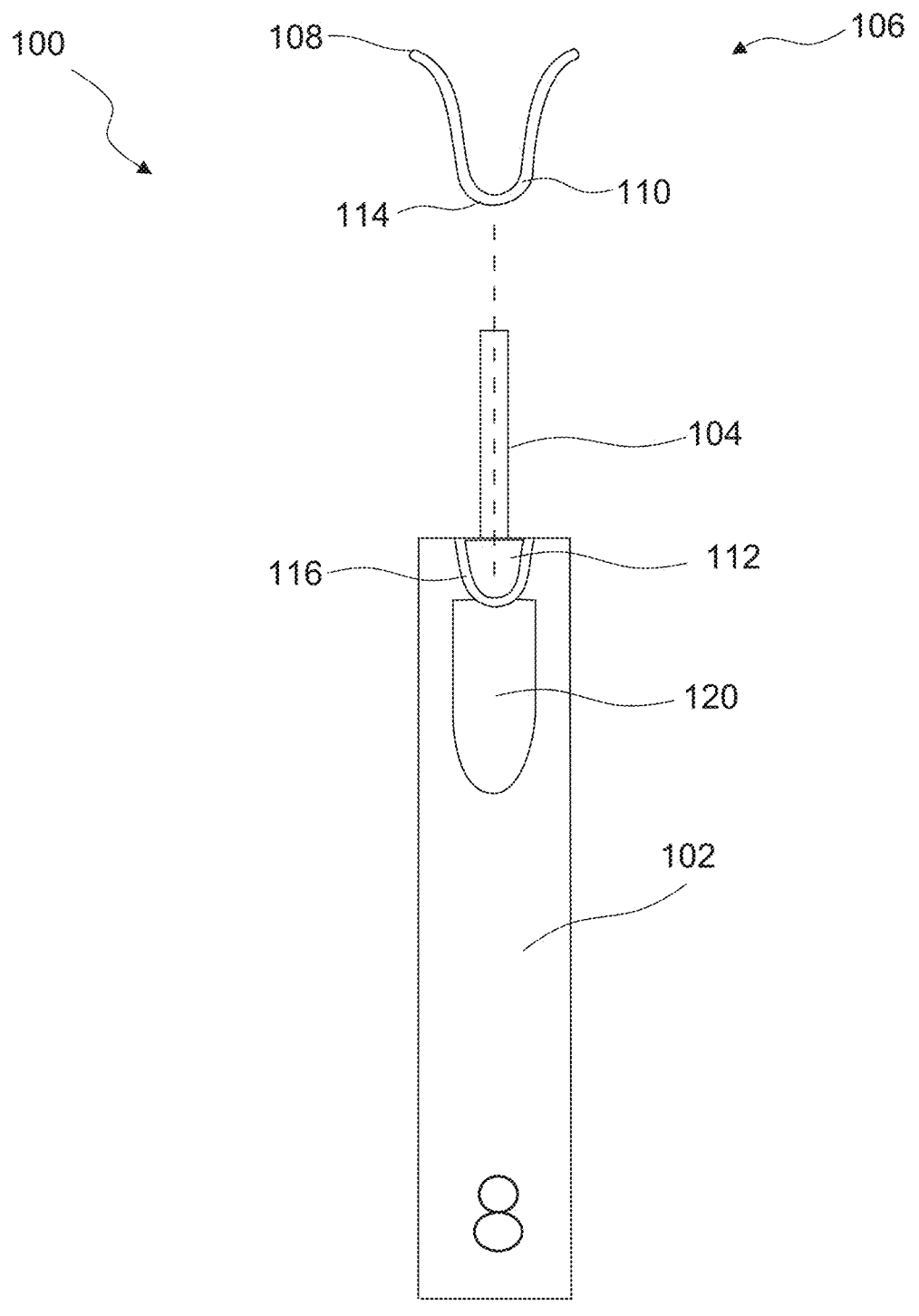
FIG. 18 is an exploded plan view of the registration instrument.
Figure 19:
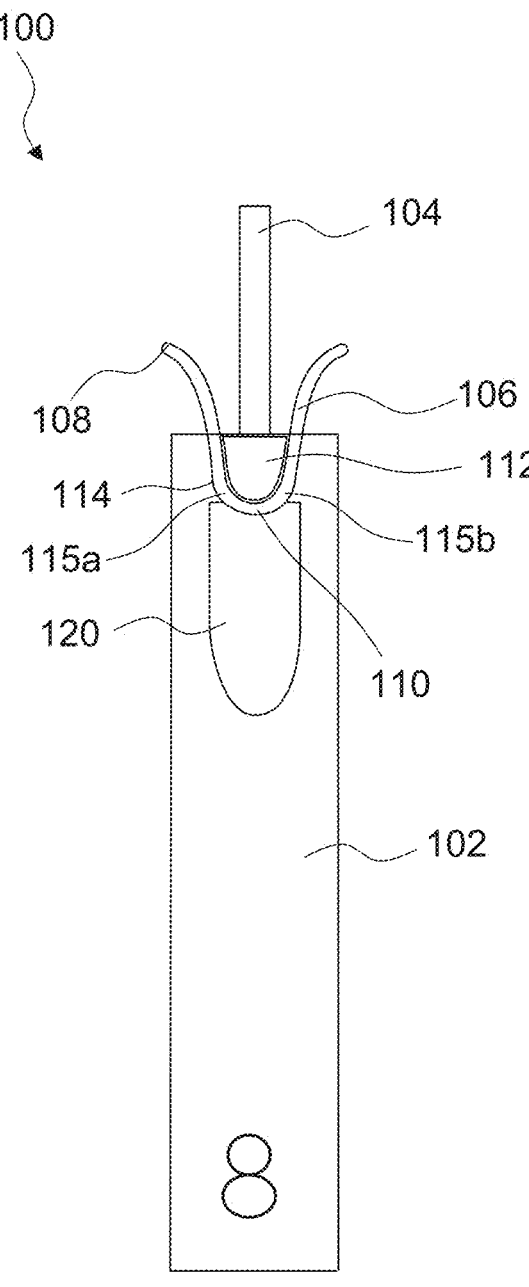
FIG. 19 is an unexploded plan view of the registration instrument.
Figure 20:
FIG. 20 is an unexploded side elevation view of the registration instrument.
Figure 20:
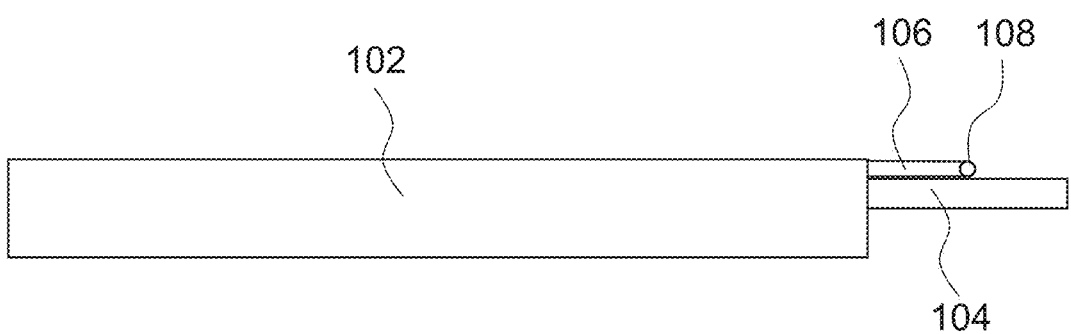

FIGS. 12 and 13 show an example of a first (face-engaging) portion 82 of a nasal mask that may be made in two portions. Similar to the example depicted in FIGS. 8 to 10, the nasal mask does not include any arms 32 and the face-engaging portion 82 is sufficiently large in surface area such that the mask stays anchored to the user's face by the magnets 22 during use. FIGS. 14 and 15 show a first (face-engaging) portion 84 of a further example nasal mask made in two portions. The mask includes a pair of face-engaging wing sections 86 outwardly extending from a nose-engaging section 88 of the mask portion 84. FIG. 16 shows a further example of a first (face-engaging) portion 90 of a nasal mask that may be made in two portions. Similar to the example depicted in FIGS. 8 to 10, the nasal mask does not include any arms 32.

The ferromagnetic members 22 advantageously cause the nasal mask 20 to be secured to the user's face in the correct position without the requirement for head straps, which significantly improves the comfort and practicality of the mask 20. The arrangement of the chamber 62 and upwardly extending hose 64 encourages natural breathing of the user. The foregoing improvements ensure a greater likelihood of long-term patient compliance and therapeutic success.

Any method steps, processes and operations described herein are not to be construed as necessarily requiring their performance in the particular order discussed or illustrated, unless specifically identified as an order of performance. It is also to be understood that additional or alternative steps may be employed.

For the purpose of this specification, the word "comprising" means "including but not limited to", and the word "comprises" has a corresponding meaning.

The above embodiments have been described by way of example only and modifications are possible within the scope of the claims that follow.

The invention claimed is:

1. A breathing assistance apparatus, comprising:
an oral appliance having at least an uppermost splint adapted to engage with a set of maxillary teeth;
a strapless positive airway pressure nasal mask; and
ferromagnetic elements or materials provided on, or incorporated into, each of the oral appliance and the nasal mask, wherein one or more of the ferromagnetic elements or materials is or are magnetic such that the nasal mask and the oral appliance are attracted to each other when the apparatus is being worn by a user of the apparatus.

2. The apparatus according to claim 1, wherein the ferromagnetic elements or materials comprise at least first and second magnetic elements or materials provided on, or incorporated into, the oral appliance and the nasal mask respectively, wherein the first and second magnetic elements or materials are relatively arranged such that opposed magnetic poles of the first and second magnetic elements or materials are attracted to one another between the nasal mask and oral appliance.

3. The apparatus according to claim 2, wherein the apparatus comprises first and second sets of magnetic elements or materials provided on, or incorporated into, the nasal mask and the oral appliance respectively.

4. The apparatus according to claim 1, wherein the magnetic elements or materials comprise neodymium magnets.

5. The apparatus according to claim 1, wherein the ferromagnetic elements or materials comprise magnetic and non-magnetic elements or materials.

6. The apparatus according to claim 1, wherein the nasal mask comprises a chin-engaging portion that comprises one or more ferromagnetic elements or materials that are attracted to one or more ferromagnetic elements or materials provided on, or incorporated into, the oral appliance.

7. The apparatus according to claim 1, wherein the nasal mask comprises:
a nose-engaging section; and
a pair of face-engaging wing sections outwardly laterally extending away from the nose-engaging section in a pair of opposed directions.

8. The apparatus according to claim 7, wherein the face-engaging wing sections comprise a pair of arms adapted to engage left and right buccal regions of the user.

9. The apparatus according to claim 8, wherein the arms are dimensioned to conform with respective shapes of the buccal regions.

10. The apparatus according to claim 8, wherein a pair of the ferromagnetic elements or materials are positioned toward respective outermost ends of the arms.

11. The apparatus according to claim 7, wherein the nose-engaging section is dimensioned to conform with a shape of a bridge of a nose of the user.

12. The apparatus according to claim 7, wherein a pair of the ferromagnetic elements or materials are positioned on respective opposed sides of the nose-engaging section.

13. The apparatus according to claim 1, wherein the oral appliance comprises uppermost and lowermost splints that engage with maxillary and mandibular teeth of the user respectively, and wherein the splints are held in relative position by one or more supports extending between the splints to provide for mandibular advancement.

14. The apparatus according to claim 13, wherein the supports of the oral appliance are configured to hold the lowermost of the splints in a fixed position relative to the uppermost of the splints to provide for the mandibular advancement.

15. The apparatus according to claim 1, wherein the nasal mask comprises:
a nose-engaging section that comprises a lowermost portion that defines a chamber underneath a pair of nostrils of the user when the user is wearing the mask, wherein the chamber is dimensioned to form an airtight seal about the nostrils; and
a hose connected to a lower end of the chamber, wherein the hose is configured to supply air upwardly from the hose into the chamber such that the air flows upwardly through the chamber into the nostrils.

16. A process for manufacturing a breathing assistance apparatus, the process comprising:
scanning an oral cavity of a person to generate oral geometric data;
scanning a face of the person to generate facial geometric data;

fabricating an oral appliance based on the oral geometric data, wherein the oral appliance comprises at least an uppermost splint adapted to engage with a set of maxillary teeth of the person;

fabricating a strapless positive airway pressure nasal mask based on the facial geometric data; and attaching or incorporating ferromagnetic elements or materials to, or into, each of the oral appliance and nasal mask, wherein one or more of the ferromagnetic elements or materials is or are magnetic such that the nasal mask and oral appliance are attracted to each other when the apparatus is being worn by the user.

17. The process of claim 16, wherein the process includes scanning maxillary and mandibular teeth of the oral cavity to produce the oral geometric data, and wherein the oral appliance is fabricated so that the oral appliance includes a lowermost splint adapted to engage with the mandibular teeth.

18. The process according to claim 17, wherein the process includes adjusting a relative position of the uppermost and lowermost splints by a titration protocol to provide for mandibular advancement.

19. The process according to claim 18, wherein the process includes:

attaching one or more sensors to the person, wherein the sensors are adapted to generate data relating to breathing behaviour of the person;

collecting the data by the sensors when the user is sleeping; and adjusting a position of the lowermost of the splints relative to the uppermost of the splints based on the data to determine the mandibular advancement.

20. The process according to claim 16, wherein the oral appliance and the nasal mask are each fabricated using an additive manufacturing process.

* * * * *